(12) United States Patent
Kortenbach

(10) Patent No.: US 7,083,636 B2
(45) Date of Patent: Aug. 1, 2006

(54) TISSUE FASTENERS AND RELATED METHODS

(75) Inventor: Juergen A. Kortenbach, Miami Springs, FL (US)

(73) Assignee: Symbiosis Corporation, Miami, FL (US)

( * ) Notice: Subject to any disclaimer, the term of this patent is extended or adjusted under 35 U.S.C. 154(b) by 314 days.

(21) Appl. No.: 10/291,252

(22) Filed: Nov. 8, 2002

(65) Prior Publication Data

US 2003/0120285 A1 Jun. 26, 2003

Related U.S. Application Data

(63) Continuation of application No. 09/871,981, filed on Jun. 4, 2001, now Pat. No. 6,551,328, which is a continuation-in-part of application No. 09/572,974, filed on May 18, 2000, now Pat. No. 6,312,437, which is a continuation of application No. 08/963,523, filed on Nov. 3, 1997, now Pat. No. 6,086,600.

(51) Int. Cl.
*A61B 17/04* (2006.01)

(52) U.S. Cl. ............... 606/220; 606/219; 24/108

(58) Field of Classification Search ............... 606/151, 606/116–117, 120, 220–221; 24/56–60, 24/103, 104–108, 94, 102 A, 102 PL, 684
See application file for complete search history.

(56) References Cited

U.S. PATENT DOCUMENTS

| | | | |
|---|---|---|---|
| 3,203,421 A * | 8/1965 | Bialick | 128/885 |
| 3,595,201 A * | 7/1971 | Oudenhoven | 40/301 |
| 3,954,108 A | 5/1976 | Davis | |
| 4,390,019 A * | 6/1983 | LeVeen et al. | 606/158 |
| 4,428,376 A * | 1/1984 | Mericle | 606/219 |
| 4,473,077 A | 9/1984 | Noiles et al. | |
| 4,485,817 A | 12/1984 | Swiggett | |
| 4,497,321 A * | 2/1985 | Fearing et al. | 606/117 |
| 4,512,345 A | 4/1985 | Green | |

(Continued)

FOREIGN PATENT DOCUMENTS

CA 2188114 4/1997

(Continued)

OTHER PUBLICATIONS

Swain et al., "An endoscopic stapling device: the development of a new flexible endoscopically controlled device for placing transmural staples in gastrointestinal tissue," *Gastrointestinal Endoscopy*, vol. 35, No. 4, Jul./Aug. 1989, pp. 338-339.

(Continued)

*Primary Examiner*—Gary Jackson
(74) *Attorney, Agent, or Firm*—Finnegan Henderson Farabow Garrett & Dunner, L.L.P.

(57) ABSTRACT

An endoscopic surgical instrument for deploying a two part fastener having a male fastener part and a female fastener part, includes a tube having a proximal end and a distal end. An end effector is coupled to said distal end of said tube and is configured to hold the male fastener part and the female fastener part in opposed relation. An actuator is coupled to said proximal end of said tube and is configured to actuate the end effector. A shearing device may be positioned proximate the end effector to shear off a tip of the male fastener part after the male and female fastener parts are moved into locking relation. In addition, the surgical instrument may include a male fastener part having a shaft with a plurality of detent positions. Further, the male fastener part may include a base and a shaft pivotally connected to the base.

28 Claims, 41 Drawing Sheets

U.S. PATENT DOCUMENTS

| | | | | |
|---|---|---|---|---|
| 4,513,746 | A | 4/1985 | Aranyi et al. | |
| 4,531,522 | A | 7/1985 | Bedi et al. | |
| 4,573,469 | A | 3/1986 | Golden et al. | |
| 4,635,634 | A | 1/1987 | Santos | |
| 4,667,767 | A * | 5/1987 | Shea et al. | 180/247 |
| 4,741,336 | A * | 5/1988 | Failla et al. | 227/181.1 |
| 4,858,608 | A | 8/1989 | McQuilkin | |
| 4,907,591 | A | 3/1990 | Vasconcellos et al. | |
| 4,919,152 | A | 4/1990 | Ger | |
| 5,088,979 | A | 2/1992 | Filipi et al. | |
| 5,100,420 | A | 3/1992 | Green et al. | |
| 5,114,065 | A | 5/1992 | Storace | |
| 5,190,203 | A | 3/1993 | Rodak | |
| 5,197,649 | A | 3/1993 | Bessler et al. | |
| 5,263,967 | A | 11/1993 | Lyons et al. | |
| 5,352,238 | A | 10/1994 | Green et al. | |
| 5,358,496 | A | 10/1994 | Ortiz et al. | |
| 5,358,510 | A * | 10/1994 | Luscombe et al. | 606/220 |
| 5,403,326 | A | 4/1995 | Harrison et al. | |
| 5,423,858 | A | 6/1995 | Bolanos et al. | |
| 5,465,894 | A | 11/1995 | Clark et al. | |
| 5,478,354 | A | 12/1995 | Tovey et al. | |
| 5,507,776 | A * | 4/1996 | Hempel | 606/219 |
| 5,571,116 | A | 11/1996 | Bolanos et al. | |
| 5,571,125 | A * | 11/1996 | Chadwick | 606/157 |
| 5,573,169 | A | 11/1996 | Green et al. | |
| 5,593,421 | A | 1/1997 | Bauer | |
| 5,676,674 | A | 10/1997 | Bolanos et al. | |
| 5,833,696 | A | 11/1998 | Whitfield et al. | |
| 5,855,565 | A | 1/1999 | Bar-Cohen et al. | |
| 5,897,562 | A | 4/1999 | Bolanos et al. | |
| 6,074,401 | A | 6/2000 | Gardiner et al. | |
| 6,086,600 | A | 7/2000 | Kortenbach | |
| 6,131,576 | A * | 10/2000 | Davis | 128/885 |
| 6,279,202 | B1 * | 8/2001 | Wojdylak et al. | 24/12 |
| 6,312,437 | B1 | 11/2001 | Kortenbach | |
| 2002/0156344 | A1 | 10/2002 | Pasricha et al. | |

FOREIGN PATENT DOCUMENTS

EP          0 770 354          5/1997

OTHER PUBLICATIONS

J. Barry McKernan, M.D., PhD, et al., "Laparoscopic Antirefllux Surgery," *The American Surgeon*, Vo. 61, pp. 530-536, Jun. 1995.

* cited by examiner

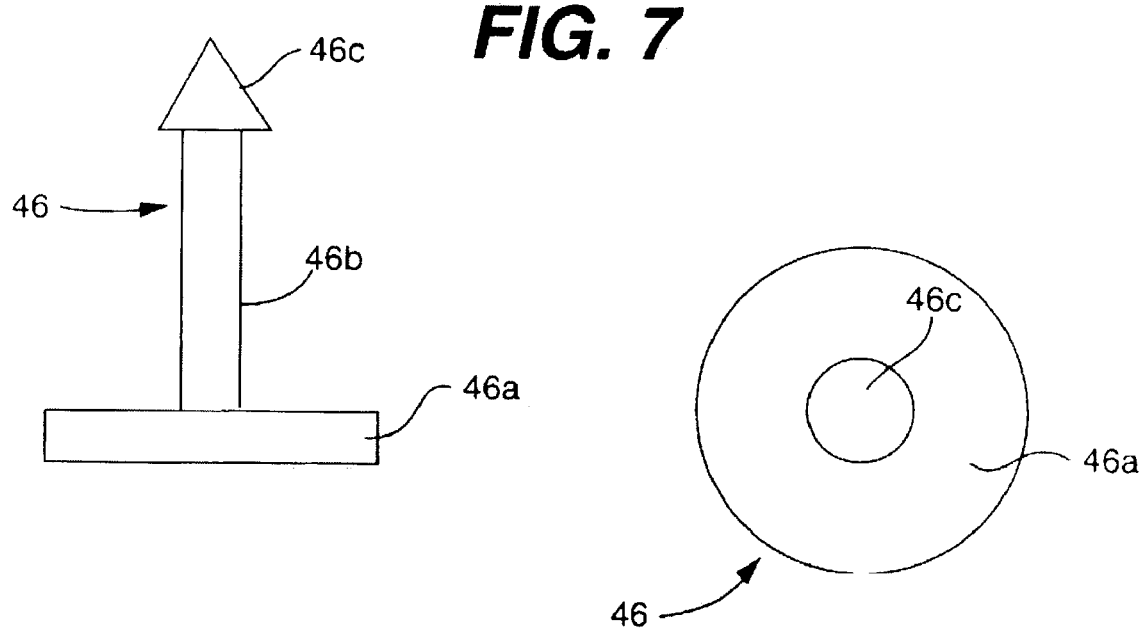
FIG. 7
FIG. 8
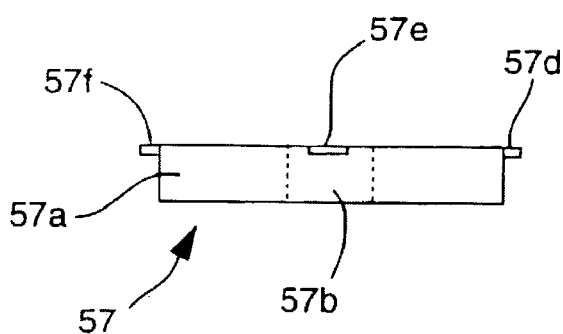
FIG. 9
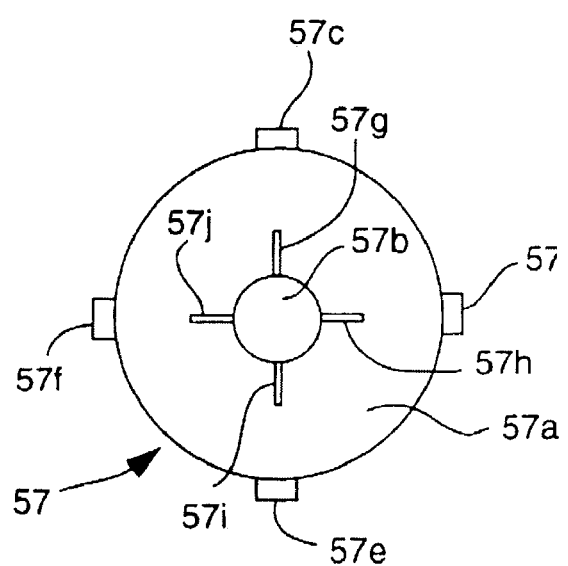
FIG. 10

TISSUE FASTENERS AND RELATED METHODS

CROSS REFERENCE TO RELATED DOCUMENTS

The present application is a continuation of application Ser. No. 09/871,981, filed Jun. 4, 2001, now U.S. Pat. No. 6,551,328 which is a continuation-in-part of U.S. patent application Ser. No. 09/572,974, filed May 18, 2000, now U.S. Pat. No. 6,312,437 which is a continuation of U.S. patent application Ser. No. 08/963,523 filed Nov. 3, 1997, now U.S. Pat. No. 6,086,600. The entire disclosure of both of these earlier applications is incorporated by reference herein.

DESCRIPTION OF THE INVENTION

1. Field of the Invention

The invention relates to an endoscopic surgical instrument. More particularly, the invention relates to a flexible instrument for the transoral invagination and fundoplication of the stomach to the esophagus.

2. Background of the Invention

Gastroesophageal fundoplication is a procedure for the treatment of gastroesophageal reflux disease (GERD), a condition in which gastric acids are regurgitated into the esophagus resulting in esophagitis, intractable vomiting, asthma, and aspiration pneumonia. The fundoplication procedure involves wrapping the fundus of the stomach around the lower end of the esophagus and fastening it in place. Traditionally, this procedure is accomplished via open surgery with the use of sutures to secure the plicated fundus of the stomach around the esophagus without penetrating (incising) the stomach.

U.S. Pat. No. 5,403,326 to Harrison et al. discloses a method of performing endoscopic fundoplication using surgical staples or two-part surgical fasteners. The procedure disclosed by Harrison et al. involves performing two percutaneous endoscopic gastrotomies (incisions through the skin into the stomach) and the installation of two ports through which a stapler, an endoscope, and an esophageal manipulator (invagination device) are inserted. Under view of the endoscope, the esophageal manipulator is used to pull the interior of the esophagus into the stomach. When the esophagus is in position, with the fundus of the stomach plicated, the stapler is moved into position around the lower end of the esophagus and the plicated fundus is stapled to the esophagus. The process is repeated at different axial and rotary positions until the desired fundoplication is achieved. While, the procedure disclosed by Harrison et al. is a vast improvement over open surgery, it is still relatively invasive requiring two incisions through the stomach. Moreover, the procedure requires the manipulation of two different tools in order to position the fundus and to secure the fundus to the esophagus.

U.S. Pat. No. 5,571,116 to Bolanos et al. discloses a non-invasive treatment of gastroesophageal reflux disease which utilizes a remotely operable invagination device and a remotely operable surgical stapler, both of which are inserted transorally through the esophagus. According to the methods disclosed by Bolanos et al., the invagination device is inserted first and is used to clamp the gastroesophageal junction. The device is then moved distally, pulling the clamped gastroesophageal junction into the stomach, thereby invaginating the junction and involuting the surrounding fundic wall. The stapler is then inserted transorally and delivered to the invaginated junction where it is used to staple the fundic wall.

Bolanos et al. disclose several different invagination devices and several different staplers. Generally, each of the staplers disclosed by Bolanos et al. has an elongate body and a spring biased anvil which is rotatable approximately 15° away from the body in order to locate the invaginated gastroesophageal junction between the body and the anvil. The body contains a staple cartridge holding a plurality of staples, and a staple firing knife. Each of the invagination devices disclosed by Bolanos et al. has a jaw member which is rotatable at least 45° and in some cases more than 90° to an open position for grasping the gastroesophageal junction. One of the chief disadvantages of the methods and apparatus disclosed by Bolanos et al. is that the stapler and the invagination device must be both be present in the esophagus at the same time. With some of the embodiments disclosed, the presence of both instruments is significantly challenged by the size of the esophagus. In all of the embodiments, the invagination device is always laterally spaced apart from the stapler. Thus, the stapler cannot staple the invaginated tissue, per se, but can only staple tissue which is laterally adjacent to the invaginated tissue. The relatively small rotational movement of the anvil of the stapler further complicates the accommodation of tissue adjacent to the invaginated tissue. In addition, surgical staples have some inherent disadvantages as compared to other fasteners. The relatively small surface area of surgical staples allows them to pass through tissue over time, thereby unfastening the tissue and allowing the staples to migrate to other parts of the body. Bolanos et al. appears to recognize this disadvantage and proposes the application of a bolster or pledger to the tissues prior to stapling. Bolanos et al. do not explain how this can be accomplished transorally using the apparatus disclosed. In addition, while Bolanos et al. make a broad reference to other types of fasteners, the substantial size constraints imposed on the apparatus which are delivered transorally would seem to prohibit any type of fastener other than the staples shown by Bolanos et al. The actuating mechanism of the device disclosed by Bolanos et al. is somewhat awkward. In particular, the stapler anvil is biased to the open position, and it is not clear whether or not the stapler anvil can be locked in a closed position without continuously holding down a lever. In addition, it appears that the staple firing trigger can be inadvertently operated before the anvil is in the closed position. This would result in inadvertent ejection of staples into the stomach or the esophagus of the patient.

SUMMARY OF THE INVENTION

Accordingly, the present invention is directed to an effector end to be used with generally known endoscopic surgical instruments. The endoscopic surgical instrument of the present invention includes a torsionally rigid but flexible tube having a proximal end and a distal end, a grasping and fastening end effector coupled to the distal end of the tube, and a manual actuator coupled to the proximal end of the tube. The grasping and fastening end effector preferably includes a separate grasper and a separate fastener. The manual actuator is coupled to the grasper and fastener of the end effector by a plurality of flexible cables which extend through the flexible tube. The tube preferably contains a lumen for receiving a manipulable endoscope and the end effector preferably includes a passage for the distal end of the endoscope. The end effector has a store for a plurality of male fastener parts, a store for a plurality of female fastener parts, a rotatable fastener head for aligning a male fastener part and a female fastener part with tissues there between, a rotatable firing member for pressing a male fastener part through the tissues and into a female fastener part, and a rotatable grasper located between the fastener head and the firing member.

According to presently preferred embodiments, the overall diameters of the flexible tube and the end effector (when the fastener head is rotated to the open position and the grasper is rotated to the closed position) do not exceed approximately 20 mm (and preferably less than 16 mm) so that the instrument may be delivered transorally to the fundus of the stomach. The end effector preferably includes a substantially cylindrical stationary part which houses the store of male fastener parts and the firing member. Male fastener parts are ejected by the firing member through a substantially radial port in the substantially cylindrical stationary part of the end effector. The rotatable fastener head is hingedly coupled to a distal portion of the stationary part of the end effector and is rotatable from a first (open) position wherein the fastener head is rotated distally away the female fastener shuttle. The presently preferred female fastener shuttle is a sliding tray which is located adjacent to the store of female fastener parts. The second biasing member pushes female fastener parts into the tray and the tray moves laterally away from the store of female fastener parts when the rotatable fastener head is moved from the open position to the closed position.

The rotatable fastener head, the firing member, and the grasper are preferably each controlled by an individual cable; and the proximal actuator includes three levers, each coupled to a respective cable, for individually operating the rotatable fastener head, the firing member, and the grasper. According to a presently preferred embodiment, the manual actuator includes a lock-out feature which prevents the inadvertent firing of male fastener members until the fastener head is rotated into the proper position. The manual actuator also includes a releasable lock for locking the grasper in the closed position.

According to one embodiment, the male fastener member is a circular disk with a central upstanding barbed projection and the female fastener member is a circular disk with a central hole engageable by the barbed projection of a male fastener member. According to another, presently preferred embodiment, the female from the stationary part to a second (closed) position wherein the fastener head is rotated proximally toward the stationary part. The store of female fastener parts is preferably contained within the fastener head and a female fastener shuttle on the fastener head moves a female fastener from the store into alignment with the substantially radial port when the fastener head is rotated to the closed position.

The presently preferred store for male fastener parts includes a longitudinal track arranged proximally of the rotatable firing member in which male fastener parts are arranged one behind the other. Male fastener parts are moved distally along the track by a first biasing member. According to one embodiment, the firing member includes a flange which blocks distal movement of male fastener parts while a male fastener part is being ejected. According to a presently preferred embodiment, a spring leaf with a pair of bent teeth engages the distal end of the next male fastener part in the track keeping it from moving off the track. When the firing member moves down to grab another male fastener part, the leaf is deflected allowing the next male fastener part to enter the firing member. The presently preferred store for female fastener parts includes an orthogonal chamber in which female fastener parts are stacked on top of each other and a second biasing member for moving the female fastener parts into a firing position. The female fastener is rectangular with a central hole engageable by the barbed projection of a male fastener member. The female member is preferably provided with a plurality of weak peripheral extensions which allow the member to be held in the shuttle tray, but forcibly removed therefrom after it is coupled to a male member.

The apparatus of the invention is advantageously utilized in a fundoplication procedure. The instrument is prepared by inserting a manipulable endoscope into the proximal end of the instrument and threading the endoscope through the lumen of the flexible tube out through the end of the end effector. With the grasper closed and the rotatable fastener head in the first (open) position, the end effector is inserted into the mouth of the patient and guided down through the esophagus into the stomach with the aid of the endoscope. When the end effector is distal of the lower esophageal sphincter, the grasper is opened and the end effector is raised toward the fundus so that the fundus and the lower end of the esophagus are located between the stationary part of the end effector and the grasper. The grasper is then closed to clamp together the tissue around the juncture of the esophagus and the fundus. With the grasper closed, the rotatable fastener head is closed, raising it up toward the fundus and lifting the fundus up against the esophagus. With the instrument in this configuration, the firing member is actuated and a male fastener member is ejected out of the radial port, through the esophagus and the fundus, and into a female fastener member which is held by the tray in the rotatable fastener head. The firing member is then returned to its initial position moving the flange or the leaf away from the male fastener store and allowing a second male fastener to be pushed onto the second rotatable member. The rotatable fastener head is moved to the open position, releasing the female fastener, and returning the tray to the store of female fasteners to receive a second female fastener. The grasper is opened and the instrument may then be repositioned and the above procedure repeated until the desired fundoplication is achieved.

According to another aspect, the invention includes an endoscopic surgical instrument for deploying a two part fastener having a male fastener part and a female fastener part. The surgical instrument includes a tube having a proximal end and a distal end. An end effector is coupled to the distal end of the tube. The end effector is configured to hold the male fastener part and the female fastener part in opposed relation. An actuator is coupled to the proximal end of the tube and the actuator is configured to actuate the end effector. According to one aspect of the invention, a shearing device may be coupled to the distal end of the tube and is configured to shear off a tip of the male fastener part after the male and female fastener parts are moved into locking relation. According to another aspect of the invention, the surgical instrument may include a male fastener part having a shaft with a plurality of detent positions. According to yet another aspect of the invention, the male fastener part may include a base and a shaft pivotally connected to the base.

Additional objects and advantages of the invention will become apparent to those skilled in the art upon reference to the detailed description taken in conjunction with the provided figures.

BRIEF DESCRIPTION OF THE DRAWINGS

FIG. 7 is an enlarged side elevation view of a male fastener part according to the invention;

FIG. 8 is an enlarged top view of the fastener part of FIG. 7;

FIG. 9 is an enlarged side elevation view of a first embodiment of a female fastener part according to the invention;

FIG. 10 is an enlarged top view of the fastener part of FIG. 9;

DESCRIPTION OF THE PREFERRED EMBODIMENTS

Figure 1:
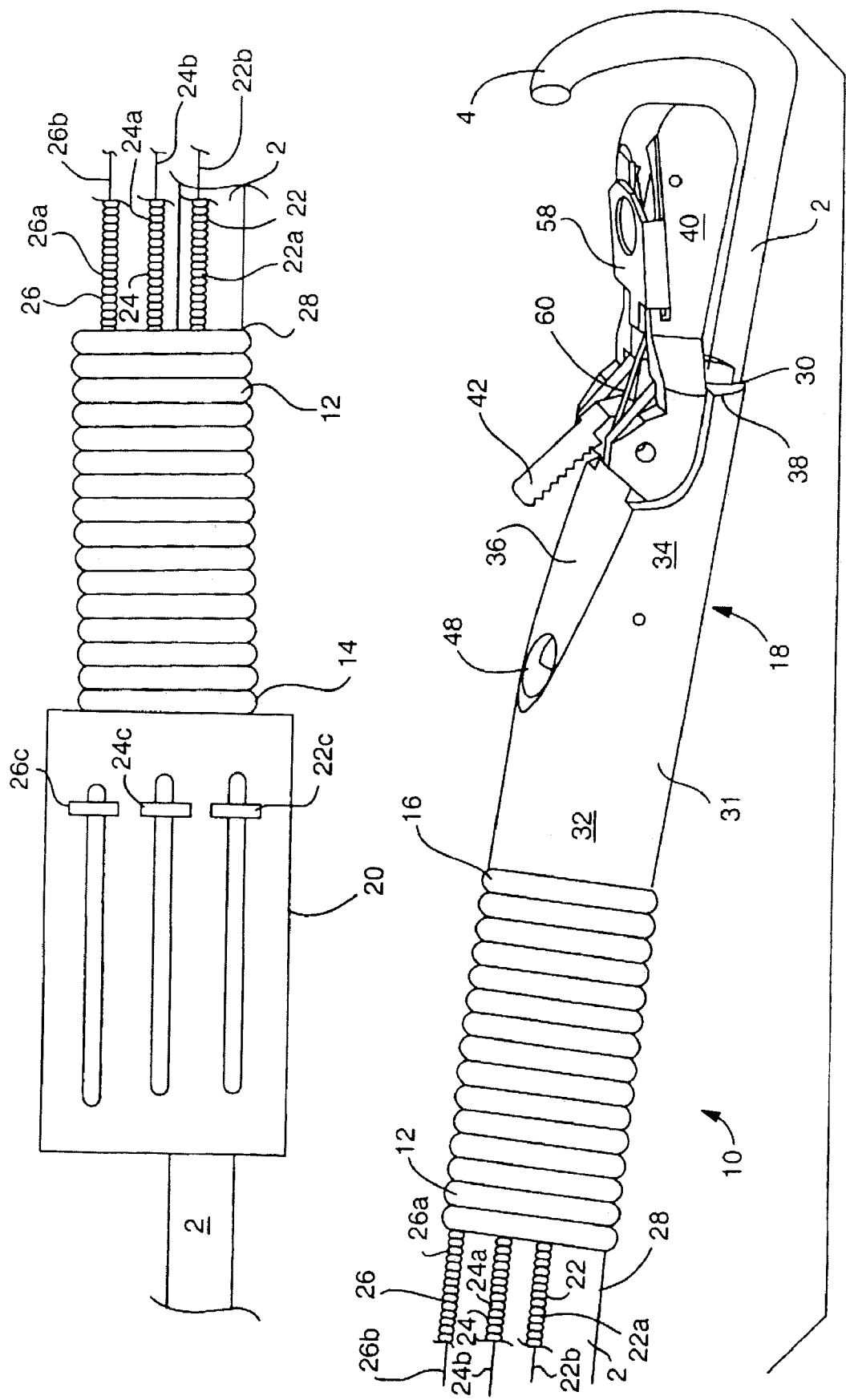
FIG. 1 is an enlarged broken perspective view of a first embodiment of a flexible endoscopic surgical instrument according to the invention with the end effector in a fully open position.

Referring now to FIGS. 1 through 4, a first embodiment of an endoscopic surgical instrument 10 includes a torsionally rigid but flexible tube 12, preferably made from polyethylene, and having a proximal end 14 and a distal end 16, a grasping and fastening end effector 18 coupled to the distal end 16 of the tube 12, and a manual actuator 20 coupled to the proximal end 14 of the tube 12. The manual actuator 20 is coupled to the end effector 18 by three flexible cables 22, 24, 26 which extend through the flexible tube 12. Each of the cables is preferably formed from an outer coil sheath 22a, 24a, 26a, and an inner pull wire 22b, 24b, 26b. The actuator 20 includes three levers 22c, 24c, 26c which are coupled to respective pull wires 22b, 24b, 26b. The tube 12 also contains a lumen 28 for receiving a manipulable endoscope 2 and the end effector 18 includes a passage 30 for the distal end 4 of the endoscope 2. Preferably, the overall diameters of the flexible tube 12 and the end effector 18 (when in the position shown in FIG. 2) do not exceed approximately 20 mm (and are preferably no more than 16 mm) so that the instrument may be delivered transorally through the esophagus to the fundus of the stomach.

The end effector 18 has a substantially cylindrical stationary member 31, a rotatable fastener head 40, and a grasper 42. The stationary member 31 has a relatively flexible proximal portion 32 and a relatively rigid distal, portion 34. The distal portion is rigid so that a store of male fastener parts and firing member can be located therein. The length of the rigid portion depends on the number of male fastener parts desired to be stored. The distal portion 34 has a flattened part 36 which angles down toward the distal end 38 of the stationary member 31. As will be described in more detail below with reference to FIGS. 5 and 6, the rotatable fastener head 40 is coupled to the distal end of the flattened portion 36 and is rotatable toward and away from the flattened portion 36 as seen best in FIGS. 2 and 3. The rotatable grasper 42 is coupled to the distal end of the flattened portion 36 proximal of the rotatable fastener head 40 and is rotatable toward and away from the flattened portion 36 as seen best in FIGS. 1 and 2. The rotatable fastener head 40 is coupled to the cable 24 so that its movement is controlled by the lever 24c and the grasper 42 is coupled to the cable 26 so that its movement is controlled by the lever 26c.

Figure 4:
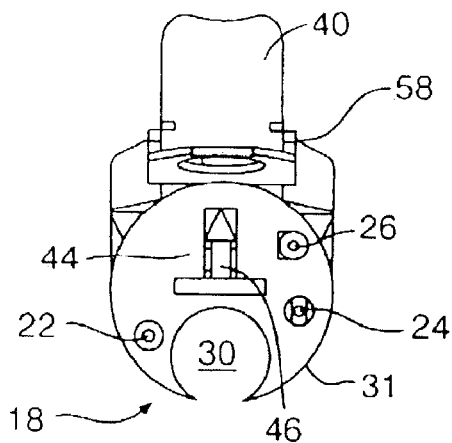
FIG. 4 is an enlarged proximal end view of the end effector removed from the instrument of FIG. 1.
Figure 5:
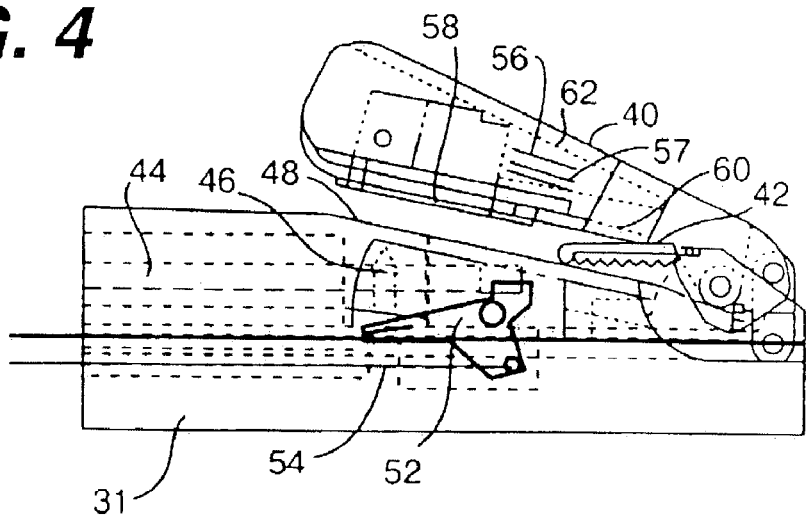
FIG. 5 is a broken enlarged transparent side elevation view of the end effector in the fully closed position.
Figure 6:
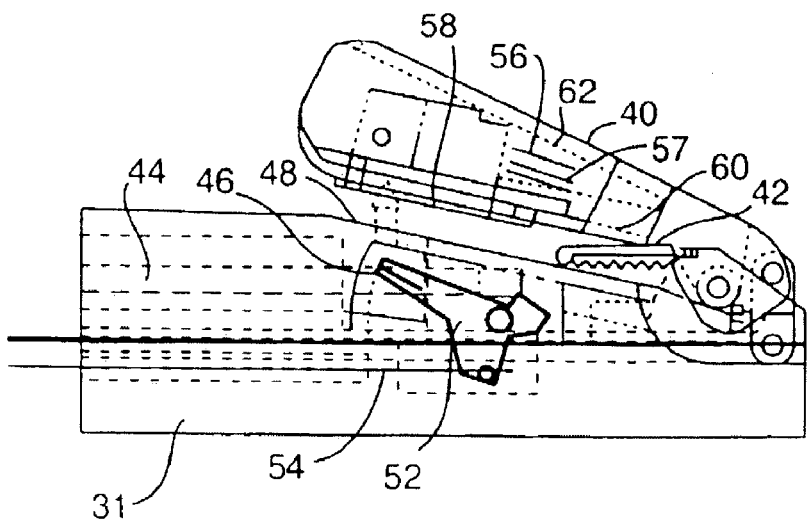
FIG. 6 is a broken enlarged transparent side elevation view of the end effector in the fully closed position with a male fastener part ejected into a female fastener part.

Referring now to FIGS. 4–6, the stationary member 31 of the end effector 18 includes a store 44 for male fastener parts, e.g. 46, and a substantially radial port 48 through which male fastener parts are ejected. As will be described in more detail below with reference to FIGS. 7 and 8, the male fasteners have a substantially T-shaped profile and the store 44 is a substantially T-shaped track which is dimensioned to hold approximately six male fastener parts. A biasing spring 50 urges the male fasteners distally along the track into position adjacent the port 48. A rotatable firing member 52 is located adjacent to the distal end of the track 44 and is coupled to the cable 22. Thus, operation of the lever 22c (FIG. 1) rotates the rotatable firing member 52 thereby ejecting a male fastener part through the port 48. A lower flange 54 on the member 52 prevents distal movement of the fastener parts in the track 44 until the member 52 is rotated back to its original position.

Referring generally to FIGS. 1–6, the rotatable fastener head 40 includes a store 56 for female fastener parts, e.g. 57, and a sliding tray 58 for moving female fastener parts out of the store 56. The sliding tray 58 is moved automatically by a wire link 60 which causes the tray to move away from the store 56 when the rotatable fastener head 40 is rotated from the open position (FIGS. 1 and 2) to the closed position (FIGS. 3–6). As will be described in more detail below with reference to FIGS. 9 and 10, according to one embodiment, the female fastener parts are generally disk shaped and are held in a stack in the store 56. A spring 62 biases the fastener parts into the tray 58 when the rotatable fastener head 40 is in the open position. The tray 58 is dimensioned such that a single fastener part is retrieved from the stack and moved in the tray to a position opposite to the port 48 when the rotatable fastener head 40 is rotated from the open position to the closed position.

Turning now to FIGS. 7–10, a presently preferred male fastener part 46 has a disk shaped base 46a, a central upstanding shaft 46b, and tapered barb 46c at the end of the shaft. According to a preferred embodiment, the base is approximately 0.3 inches in diameter and approximately 0.040 inches thick, the upstanding member is approximately 0.140 inches tall, and the barb is approximately 0.10 inches long. A first embodiment of a female fastening member 57 is a substantially flat disk 57a, having a central hole 57b, and four radially outward extending peripheral tabs 57c–57f. Four radial strain relief slits 57g–57j are preferably provided adjacent to the hole 57b. The female fastener is approximately 0.3 inches in diameter and approximately 0.040 inches thick. Both the male fastener and the female fastener parts are made from biocompatible polymers. The barb 46c, the shaft 46b, and the hole 57b are dimensioned such that the barb may be forced through the hole to lock the fastener parts together, but that once locked together, the parts will not easily separate. The peripheral tabs 57c–57f are dimensioned such that they hold the female fastener part in the sliding tray prior to being locked together with the male fastener part, but that they allow the female fastener part to be pulled out of the tray after it is locked together with the male fastener part. For example, the tabs are thin enough to bend, flex, or shear off when the female fastener part is pulled out of the tray.

Figure 2:
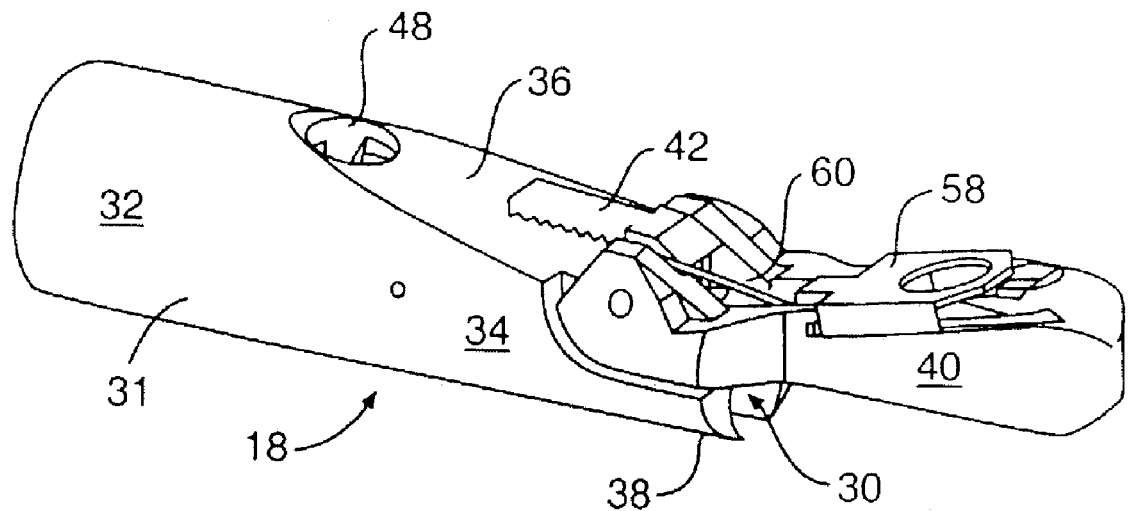
FIG. 2 is an enlarged broken perspective view of the distal end of the instrument of FIG. 1 with the grasper of the end effector in a closed position.
Figure 3:
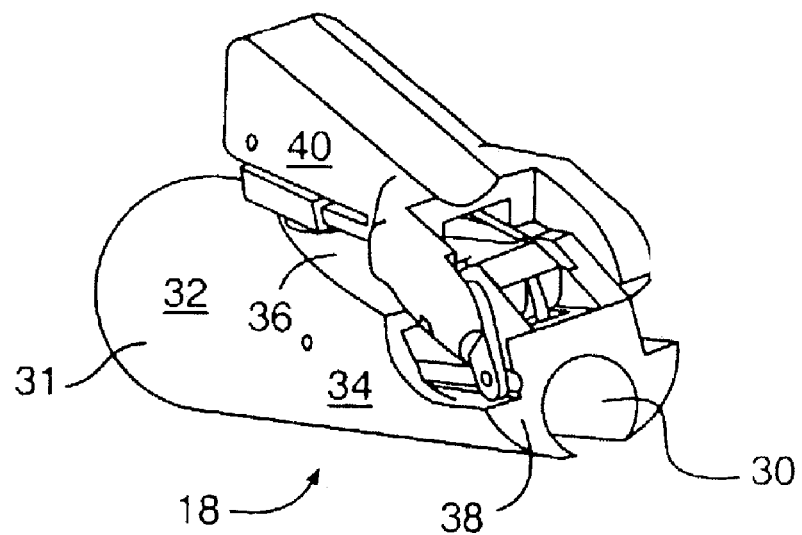
FIG. 3 is an enlarged broken perspective view of the distal end of the instrument of FIG. 1 with the end effector in a fully closed position.
Figure 11:
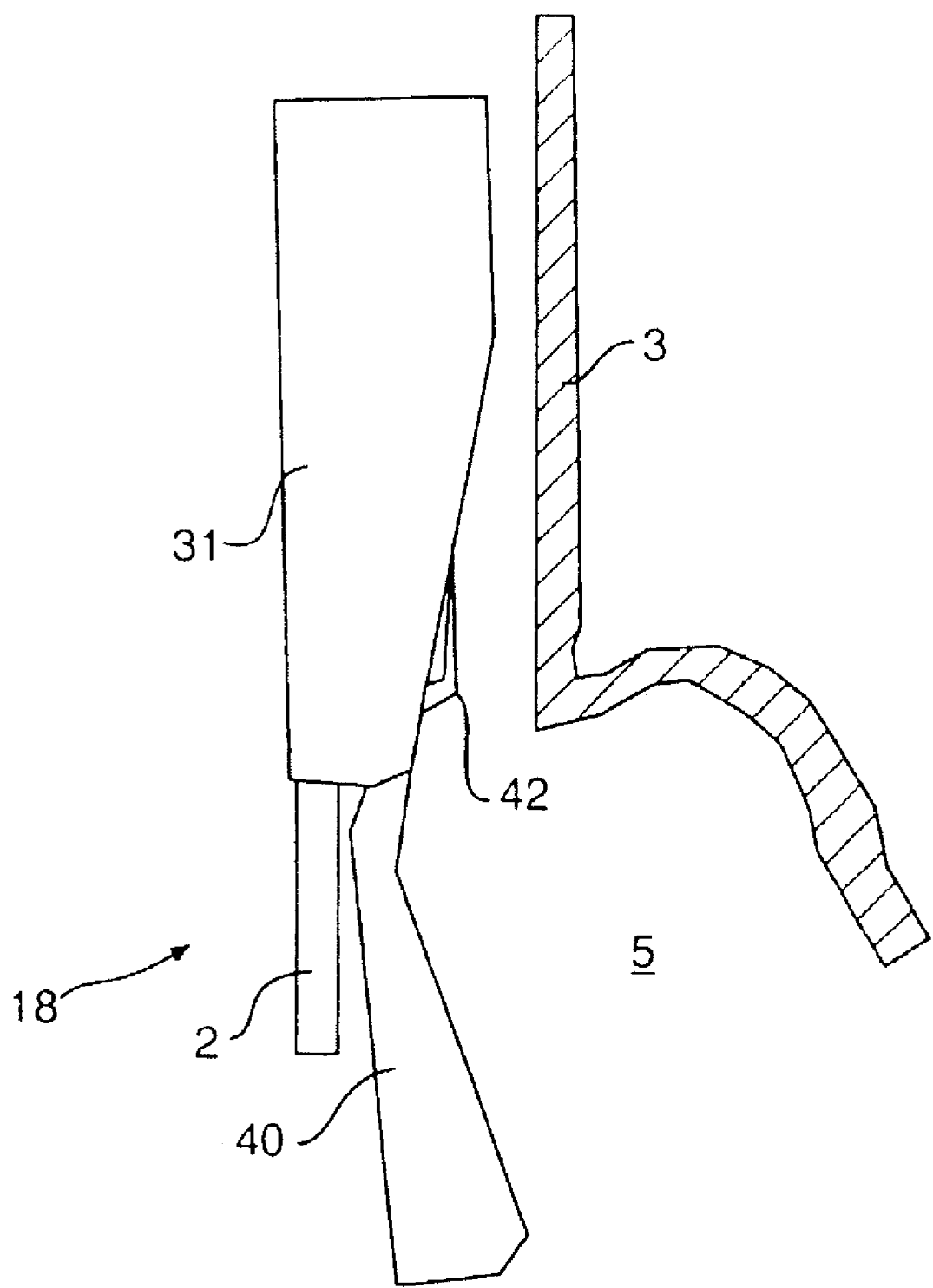
FIG. 11 is an enlarged schematic view of the distal end of the instrument of FIG. 1 adjacent the gastroesophageal junction in a first operative position.
Figure 12:
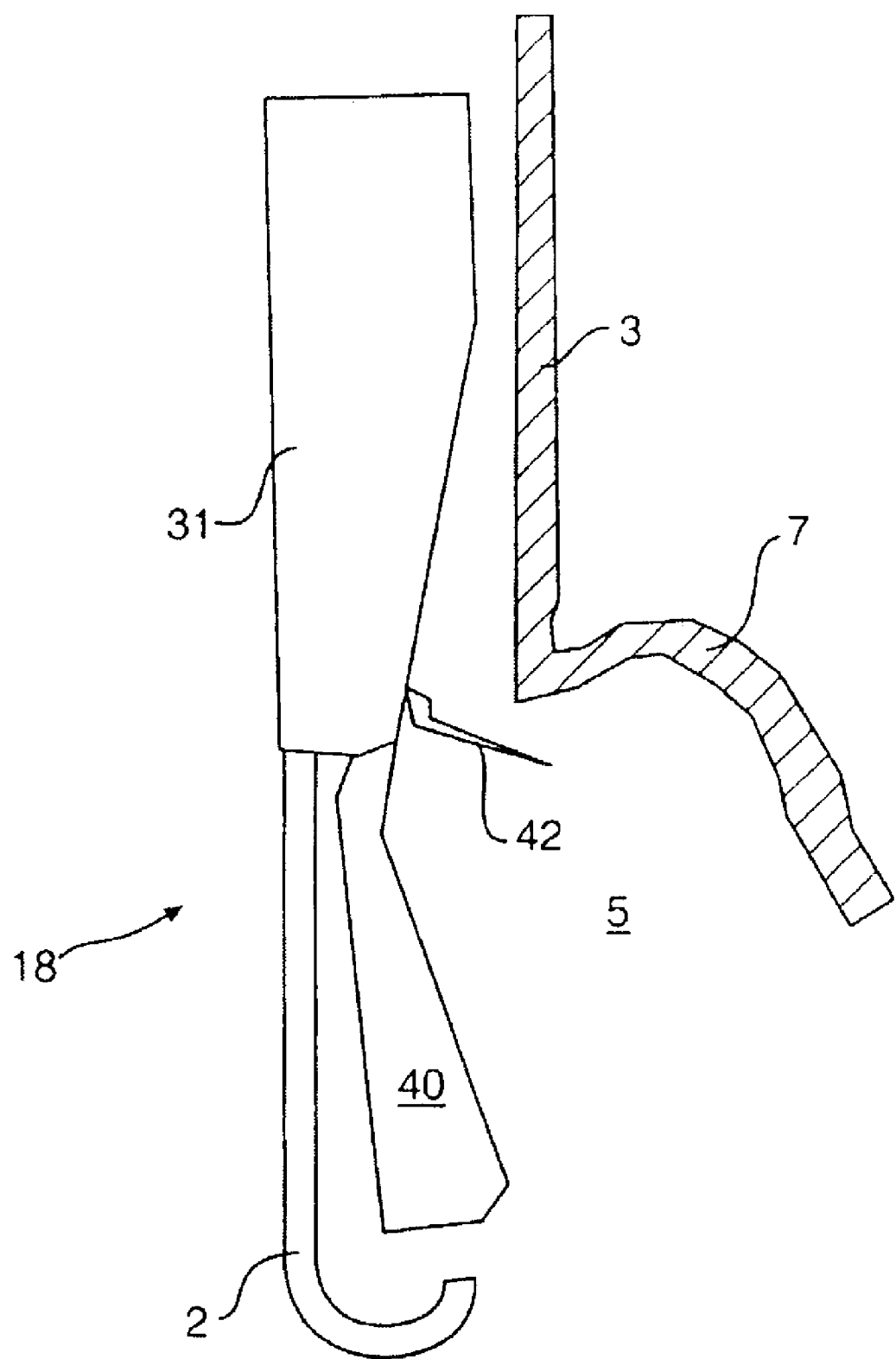
FIG. 12 is a view similar to FIG. 11 of the instrument in a second operative position.
Figure 13:
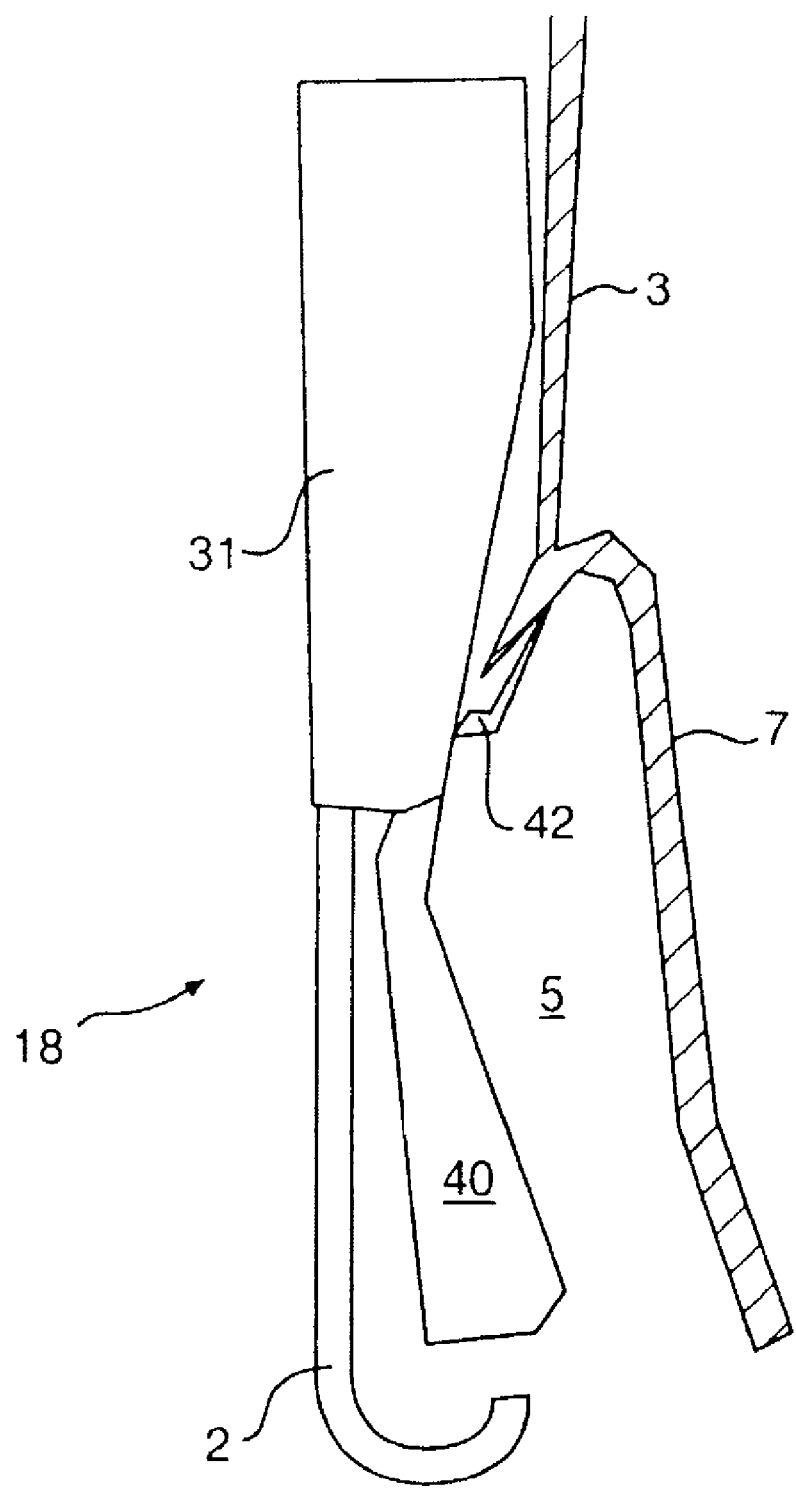
FIG. 13 is a view similar to FIG. 11 of the instrument in a third operative position.
Figure 14:
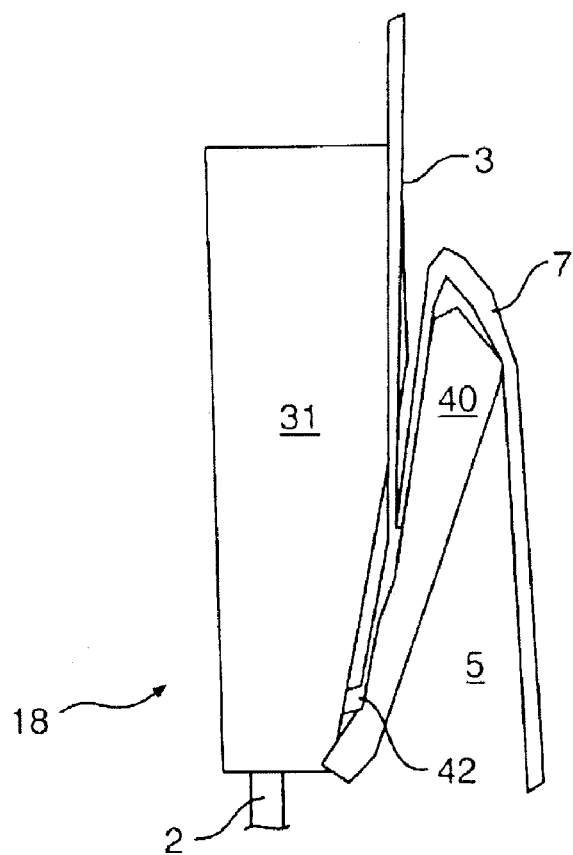
FIG. 14 is a view similar to FIG. 11 of the instrument in a fourth operative position.
Figure 15:
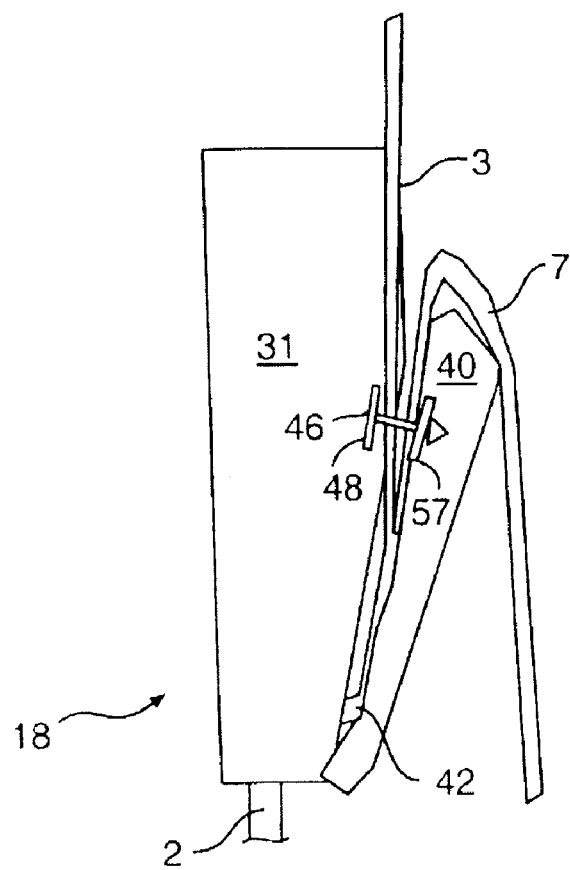
FIG. 15 is a view similar to FIG. 11 of the instrument in a fifth operative position.
Figure 16:
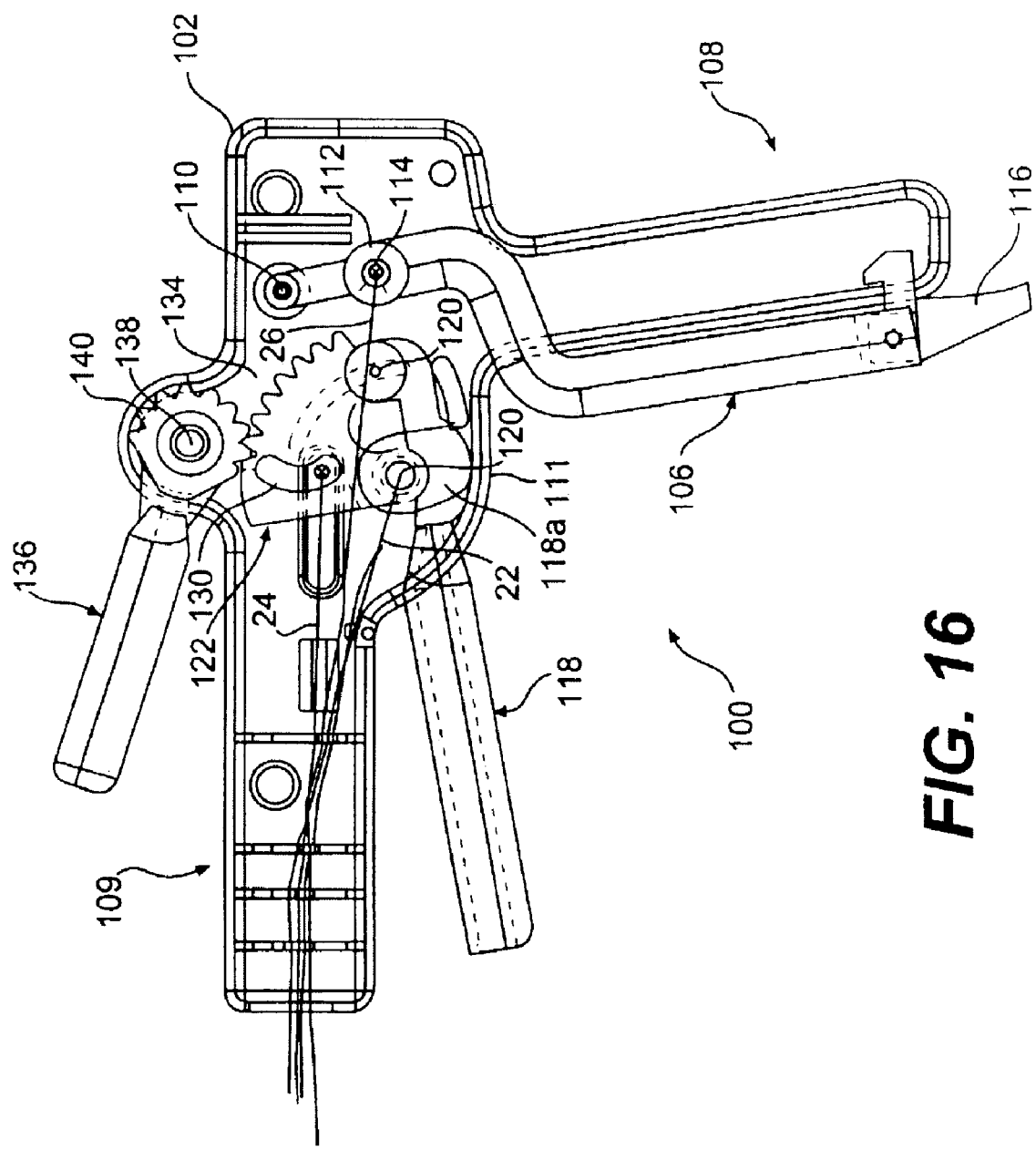
FIG. 16 is a side elevation view of one side of a presently preferred manual actuator in a first operative position (grasper closed and fastener head open) with the near side of the casing removed.
Figure 17:
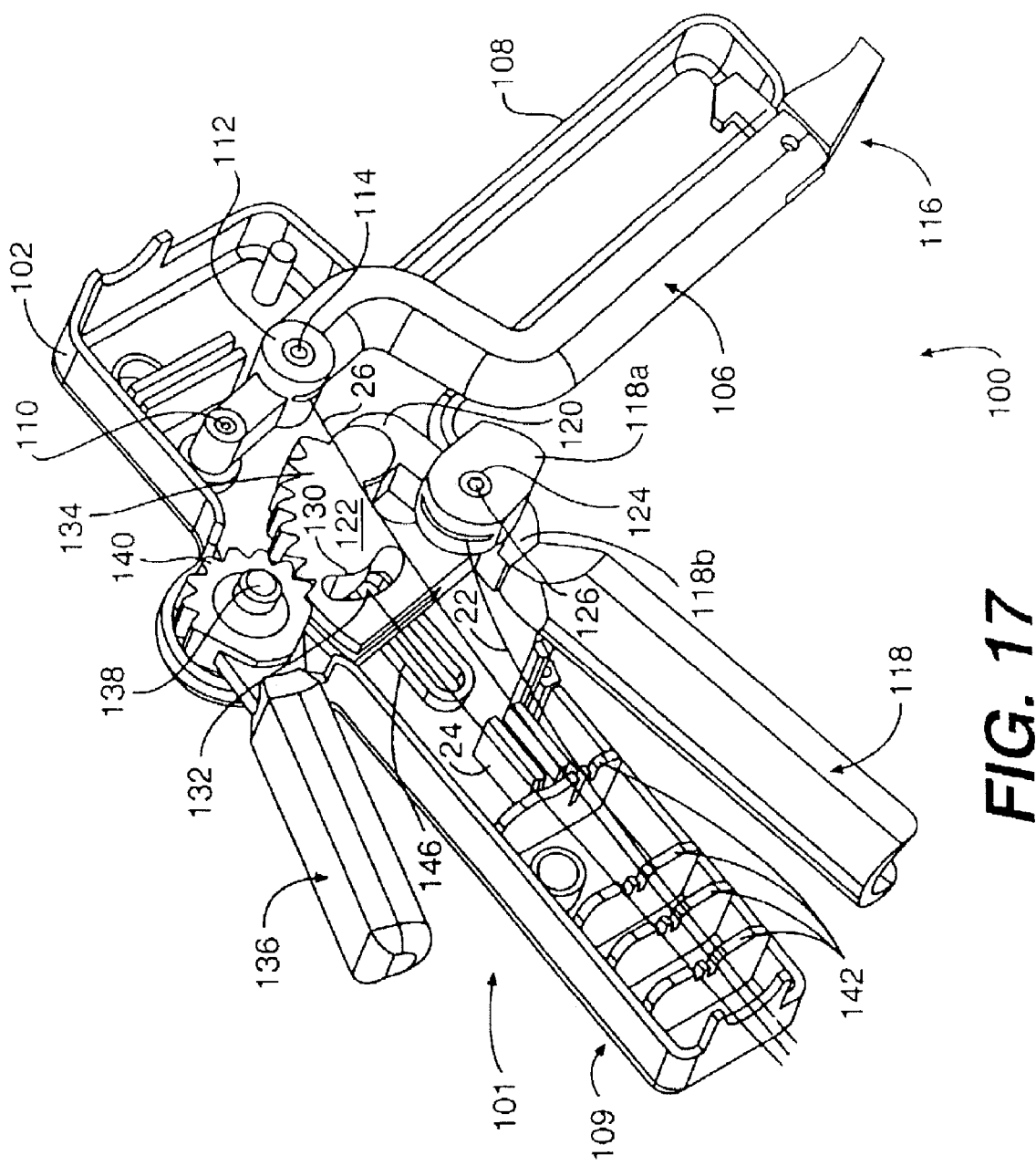
FIG. 17 is an isometric view of one side of the actuator of FIG. 16 with the near side of the casing removed.
Figure 18:
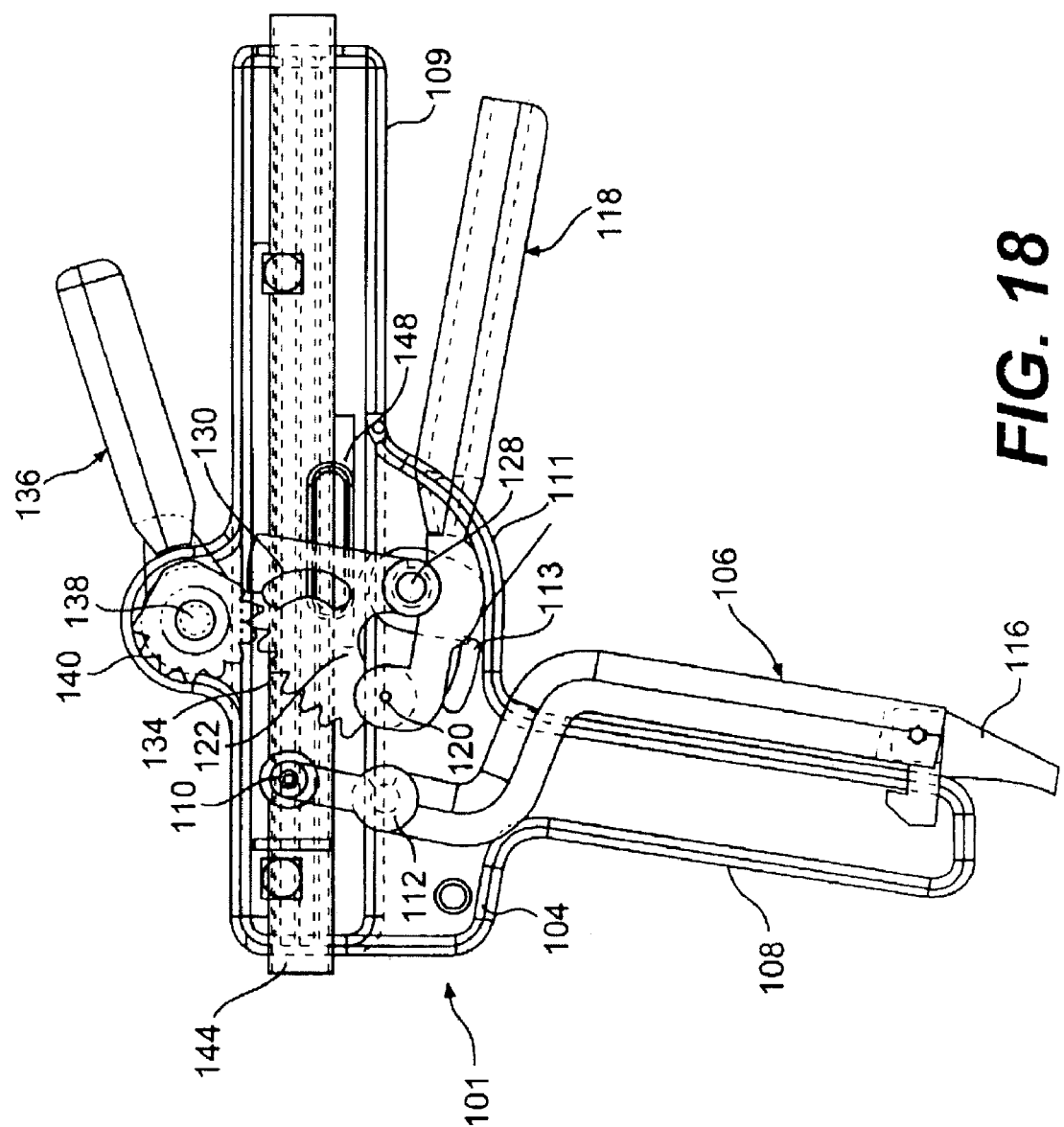
FIG. 18 is a side elevational view of the other side of the actuator of FIG. 16 with the near side of the casing removed.
Figure 19:
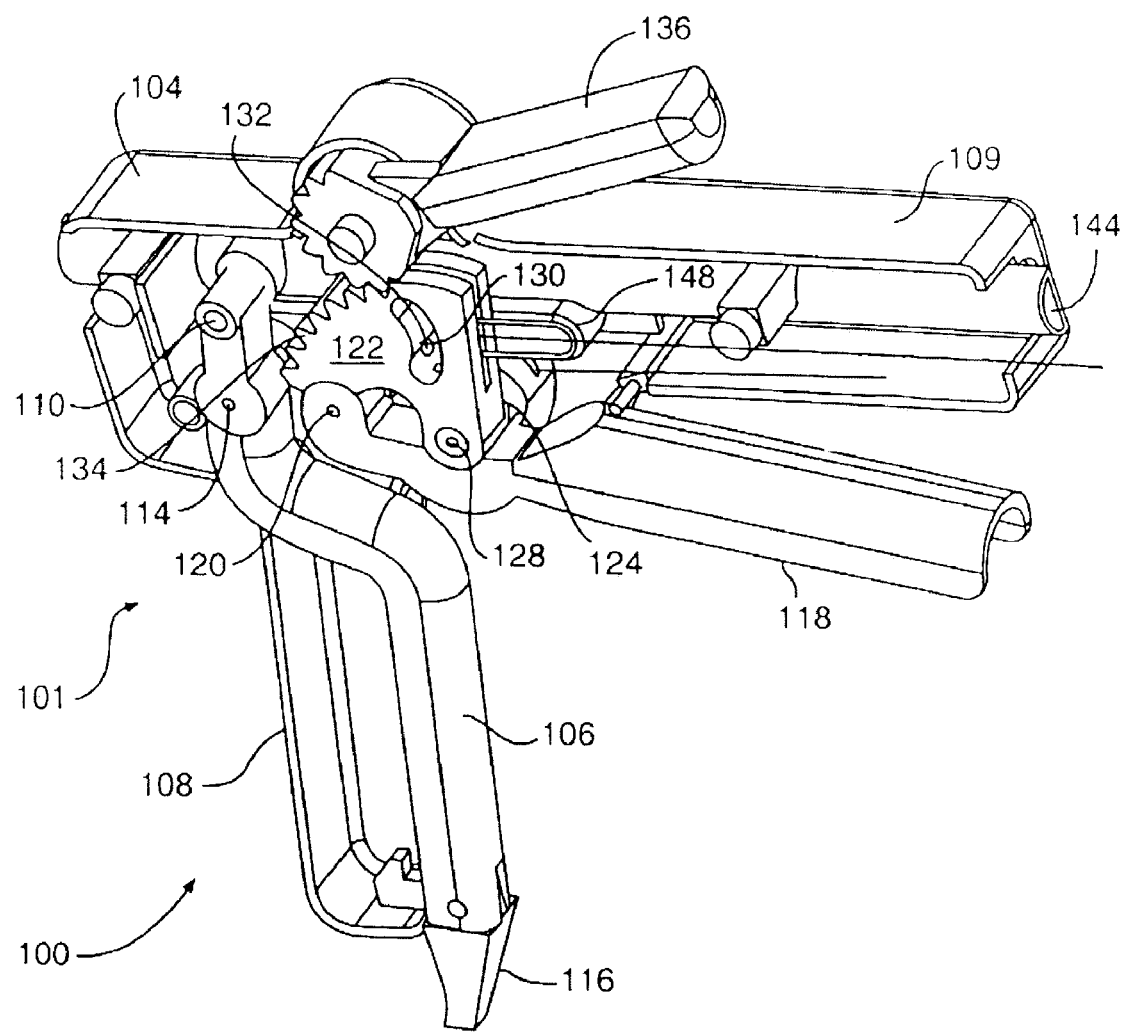
FIG. 19 is an isometric view of the other side of the actuator of FIG. 16 with the near side of the casing removed.

As mentioned above, the instrument of the invention is advantageously utilized in a fundoplication procedure. With reference now to FIGS. 1, 2 and 11–15, the instrument 10 is prepared by inserting a manipulable endoscope 2 into the proximal end of the instrument and threading the endoscope through the lumen of the flexible tube 12 out through the end of the end effector 18. With the grasper 42 closed and the rotatable fastener head 40 in the first (open) position (as shown in FIGS. 2 and 11, the end effector 18 is inserted into the mouth of the patient and guided down through the esophagus 3 into the stomach 5 with the aid of the endoscope 2. When the grasper 42 and the rotatable fastener head 40 are distal of the fundus 7, the grasper 42 is opened as shown in FIG. 12 and the end effector is raised toward the fundus 7 so that the fundus and the lower end of the esophagus 3 are located between the stationary part 31 of the end effector and the grasper 42. The grasper 42 is closed to hold the gastroesophageal junction as shown in FIG. 13. The rotatable fastener head 40 is then rotated to the closed position, raising it up toward the fundus 7 and lifting the fundus 7 up against the esophagus 3 as shown in FIG. 14. With the instrument in this configuration, the rotatable firing member (52 in FIGS. 5 and 6) is actuated and a male fastener member 46 is ejected out of the radial port 48, through the esophagus 3 and the fundus 7, and into a female fastener member 57 as shown in FIG. 15. The rotatable firing member is then returned to its original position, moving the flange 54 away from the male fastener store 44 and allowing a second male fastener to be pushed onto the second rotatable member 52. The rotatable fastener head 40 is moved to the open position, releasing the female fastener, and returning the tray to the store of female fasteners to receive a second female fastener. The grasper 42 is opened and the instrument may then be repositioned and the above procedure repeated until the desired fundoplication is achieved.

FIGS. 16 through 24 show a presently preferred manual actuator 100, according to the invention, which is provided with a lock-out feature to prevent the inadvertent firing of a male fastener member before the rotatable fastener head is in the proper position and with a lockable lever for holding the grasper in the closed position. Referring now to FIGS. 16–20, and as seen best in FIGS. 17 and 19, the actuator 100 has a generally pistol-shaped housing 101 which is formed from two mating halves 102, 104. By generally pistol-shaped, it is meant that the housing has a grip portion 108 and a barrel portion 109. Three levers (106, 118, 136) and a toothed cam (122) are rotatably mounted within the housing.

The first lever 106 is mounted adjacent to the gripping portion 108 of the housing and is pivotally coupled at its upper end to the housing by a pin 110. A slotted throughbore 112 in the lever 106 is located below the pin 110. The slotted throughbore 112 receives the proximal end of cable 26 (which controls the grasper) and the cable is attached to the lever 106 by a crosspin 114. The lower end of the lever 106 is provided with a spring biased latch 116 which is operatively engageable with a notch (not shown) in the housing.

The second lever 118 is pivotally coupled at one end 120 to the proximal end of the toothed cam 122. The second lever 118 is also provided with a slotted throughbore 124 which receives the proximal end of cable 22 (which controls the fastener firing member). The proximal end of the cable 22 is coupled to the lever 118 by a crosspin 126 in the slotted throughbore 124. The slotted throughbore 124 is located in a portion 118a of the lever 118 which is broader than an immediately adjacent portion 118b. A locking stop 113 is provided in housing half 104 (FIG. 18) which blocks movement of the broad portion 118a of the lever as described in more detail below.

The toothed cam 122 is rotatably coupled to one portion 102 of the housing by a pin 128 which is located between the grip portion 108 and the barrel portion 109 of the housing. This portion of the housing is provided with a slotted wall 111 (FIG. 16) through which the first and second levers 106, 118 exit the housing. The slot in the wall 111 is dimensioned to allow passage of the portion 118b of the lever 118 and may be dimensioned to prevent the passage of the broader portion 118a. The cam 122 has a distal curved slotted throughbore 130 which receives the proximal end of cable 24 (which controls the rotatable fastener head). The proximal end of cable 24 is coupled to the cam 122 by a crosspin 132 which rides in the curved throughbore 130. The cam 122 is provided with a plurality of peripheral teeth 134 which extend along a curved path from the proximal end of the cam where the lever 118 is coupled to it, to a point adjacent to the curved throughbore.

The third lever 136 is rotatably mounted above the cam 122 by a pin 138 and is provided with a plurality of radial teeth 140 which engage the teeth 134 of the cam 122.

The housing 101 is also provided with a plurality of cable guides 142 (FIG. 17) in the barrel portion 109 of the housing half 102 and an endoscope receiving tube 144 (FIG. 18) in the barrel portion 109 of the housing half 104. In addition, the housing halves 102,104 are provided with longitudinal guide slots 146,148 which engage the crosspin 132 and guide its motion in a longitudinal direction.

The operation of the actuator 100 is described in sequence with reference to FIGS. 16–24 and with reference to the presently preferred end effector configuration of FIGS. 25–31 which are discussed in more detail below. FIGS. 16–19 show the positions of the levers 106 and 136 when the grasper is closed and the fastener head is opened (see also FIG. 25). In this position of lever 136, the lever 118 is positioned so that it is impossible to move the lever 118 to fire a male fastener. In particular, the distal location of lever 136 has caused the radial teeth 140 to rotate the cam 122 proximally which has moved the pivot point 120 of the lever 118 to a position proximal of its broad portion 118a. In order to move the lever 118, the broad portion 118a needs to pass the stop 113 (FIG. 18) which prevents its movement. In addition, since the lever 118 must rotate about the pivot point 120, the portion 118a needs to exit the slot 111 in the housing. However, as described above, the slot may be dimensioned to prevent this movement. With the levers in the positions shown in FIGS. 16–19, the instrument is in the proper orientation for delivery through the esophagus. It will also be appreciated that the positions and locations of the levers are easy to understand and provide intuitive indication of the positions of the parts of the end effector. For example, the lever 106 is "closed" relative to the grip 108 indicating that the grasper is closed. The lever 136 is approximately 180° forward indicating that the fastener head is rotated forward (distally) approximately 180°. The lever 118, which is most like the trigger portion of the pistol shaped actuator is raised up and out of the way where it cannot be pulled.

Figure 20:
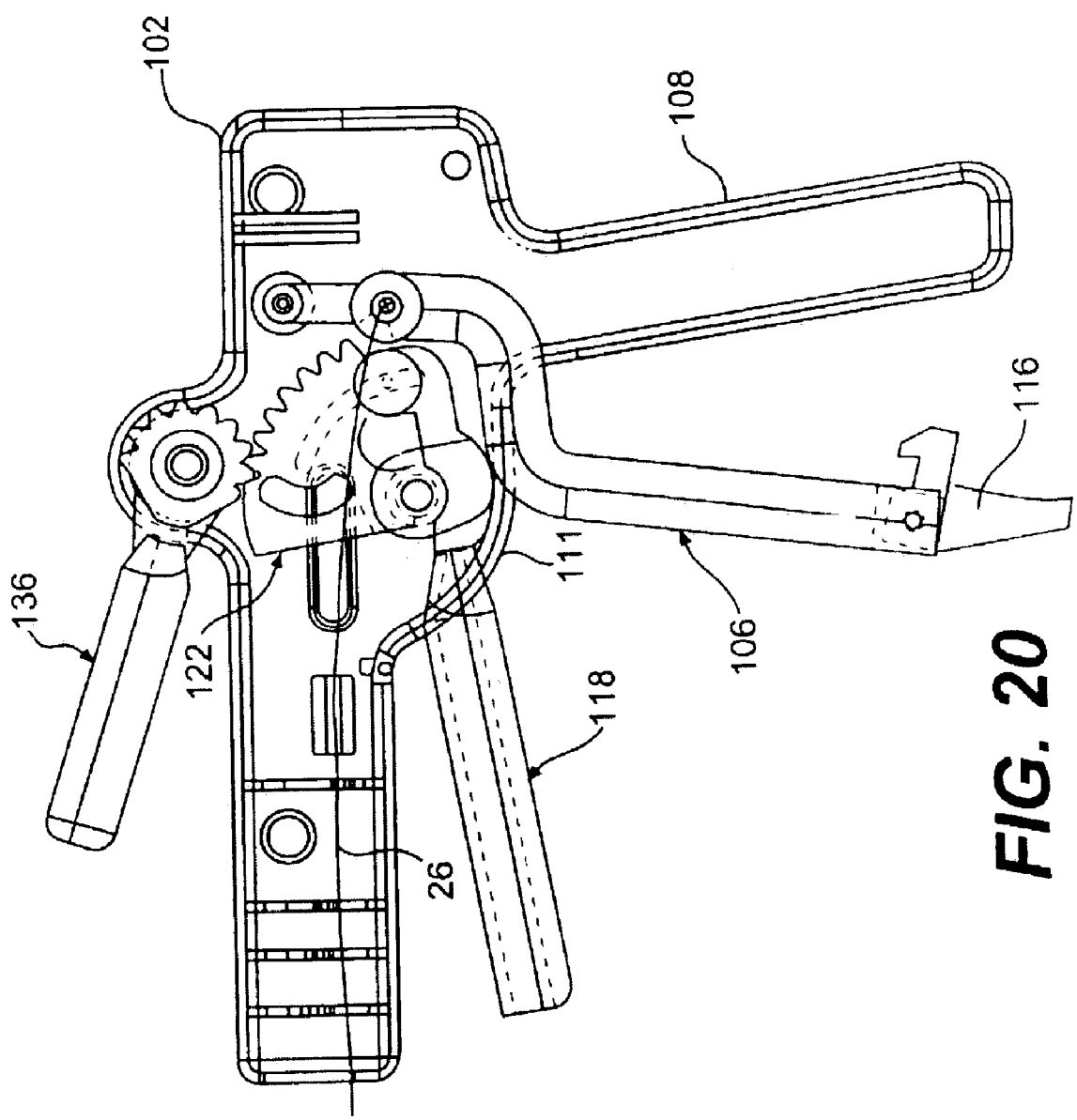
FIG. 20 is a view similar to FIG. 16 with the actuator in a second operative position (grasper open and fastener head open)

After the end effector is in place at the surgical site, the grasper is opened (to the position shown in FIG. 26) by releasing the latch 116 and moving the lever 106 distally as shown in FIG. 20; thereby moving cable 26 which is attached to the grasper 206. After the grasper has been properly positioned, the lever 106 is moved back and the latch 116 holds the grasper locked closed (in the position shown in FIG. 25).

Figure 21:
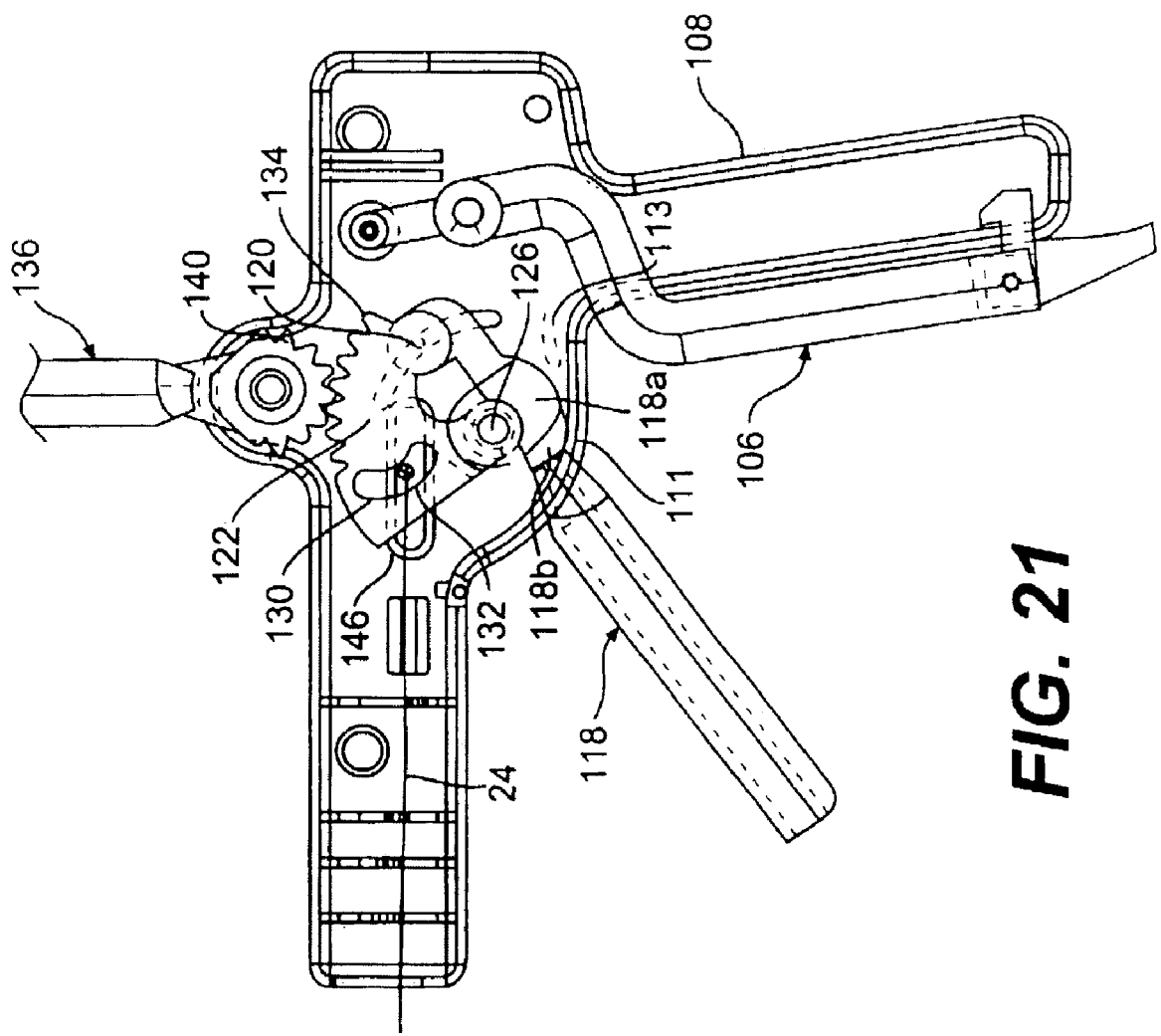
FIG. 21 is a view similar to FIG. 16 with the actuator in the midpoint a third operative position (grasper closed and fastener head partially closed)
Figure 22:
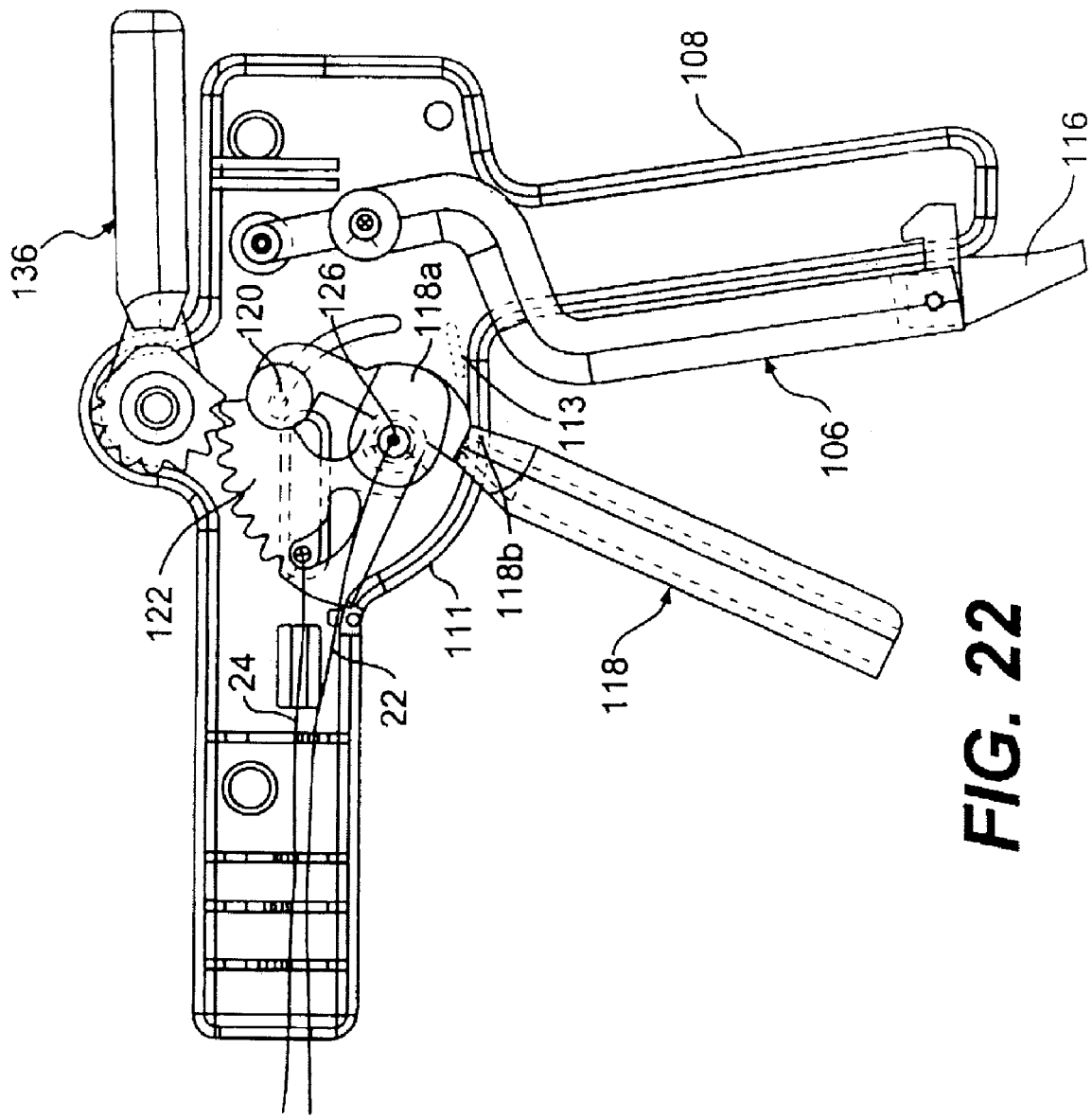
FIG. 22 is a view similar to FIG. 16 with the actuator in a fourth operative position (grasper closed and fastener head closed)

The rotatable fastener head is now closed (to the position shown in FIGS. 27–30) by rotating the lever 136 proximally which is shown in two stages in FIGS. 21 and 22. As seen in comparing FIGS. 20, 21, and 22, as the lever 136 is rotated proximally, the teeth 140 on the lever 136 engage the teeth 134 on the cam 122 causing the cam 122 to rotate distally. This action causes the curved slot 130 to rotate in a manner which forces the cross pin 132 to move distally in the slots 146, 148. Movement of the crosspin 132 moves the cable 24 distally causing the fastener head to close. At the same time, the pivot point 120 of the lever 118 is rotated above the broad portion 118a of the lever 118. This moves the broad portion 118a above the stop 113 and places the lever 118 in a position where the broad portion 118a does not need to exit the slot 111 and can freely pass alongside the stop 113. As shown in FIG. 22, the lever 118 is now operable to fire a male fastener. It will be appreciated that, until the fastening head is completely closed, movement of the firing lever 118 to pull the cable 22 is prevented by the stop 113. In addition, it will be appreciated that the crosspin coupling 126 remains stationary as the cam 122 causes the lever 118 to be rotated about this pin.

Figure 23:
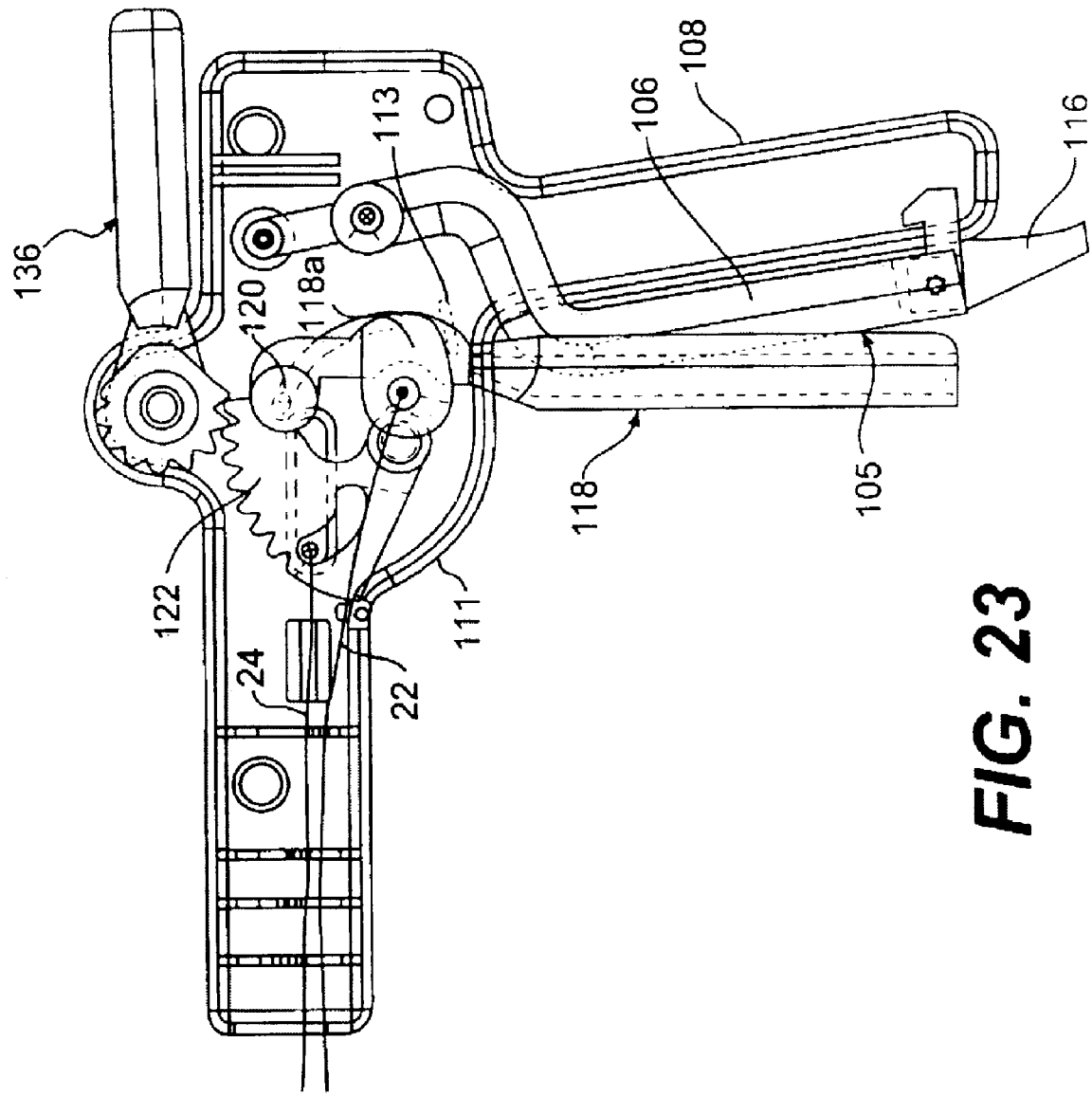
FIG. 23 is a view similar to FIG. 16 with the actuator in a fifth operative position (grasper closed, fastener head closed, and male fastener part fired)
Figure 24:
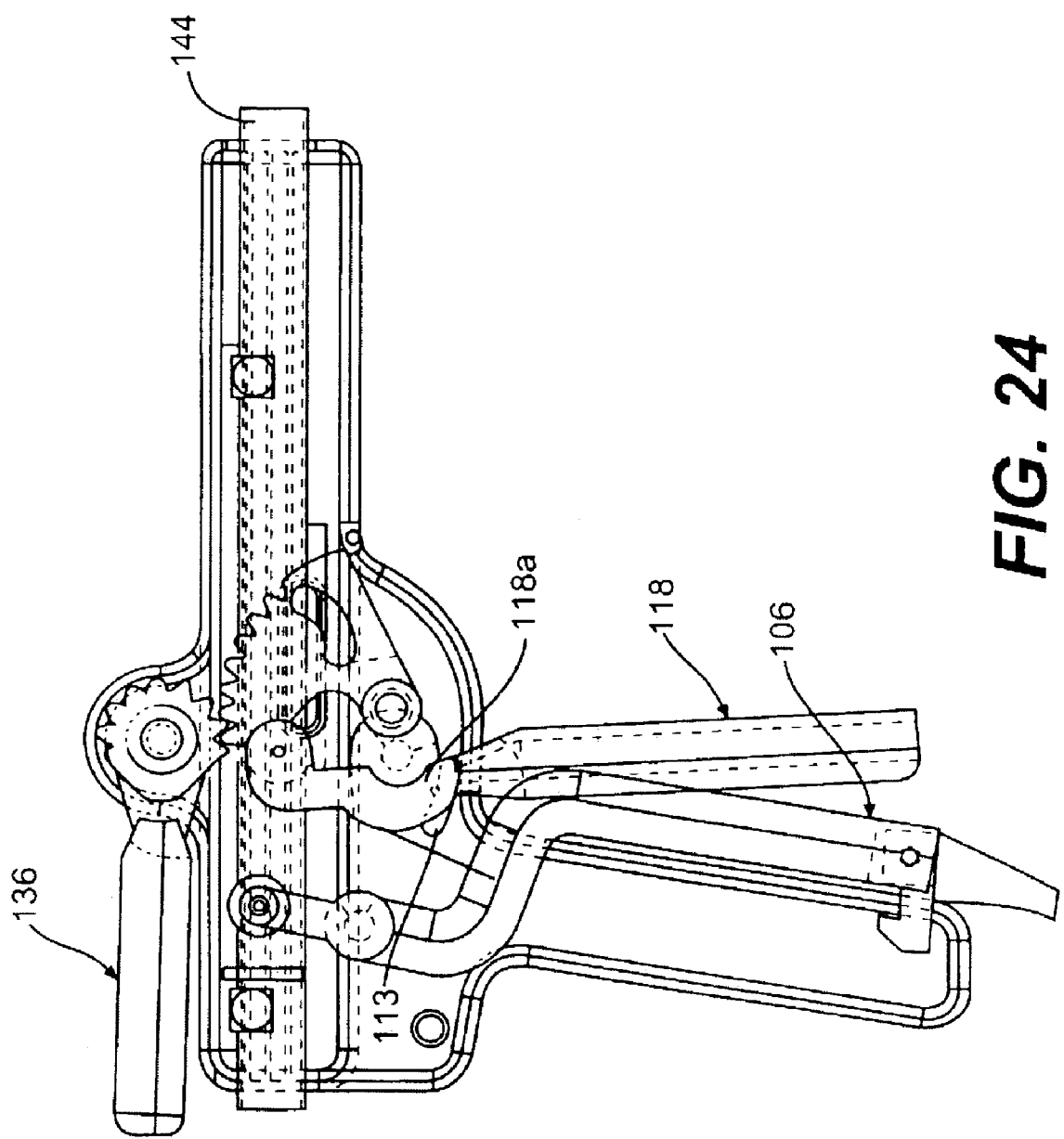
FIG. 24 is a view similar to FIG. 21 of the other side of the manual actuator.
Figure 25:
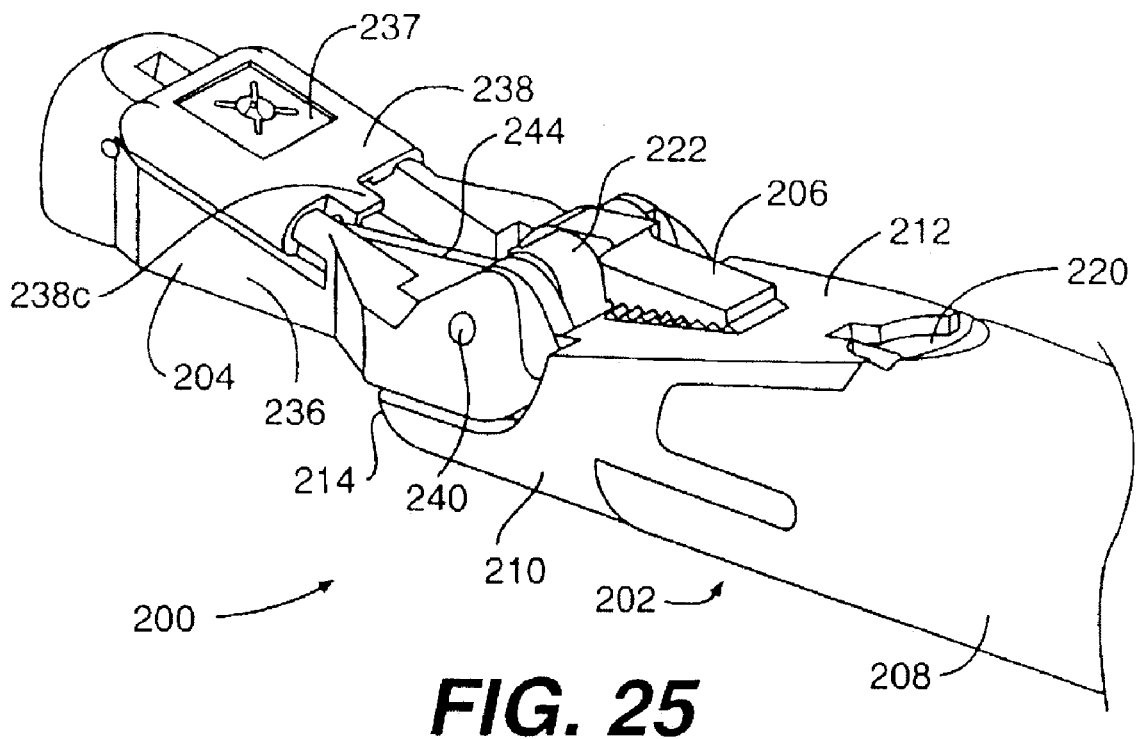
FIG. 25 is a perspective view of a presently preferred embodiment of the end effector in a first operative position.
Figure 26:
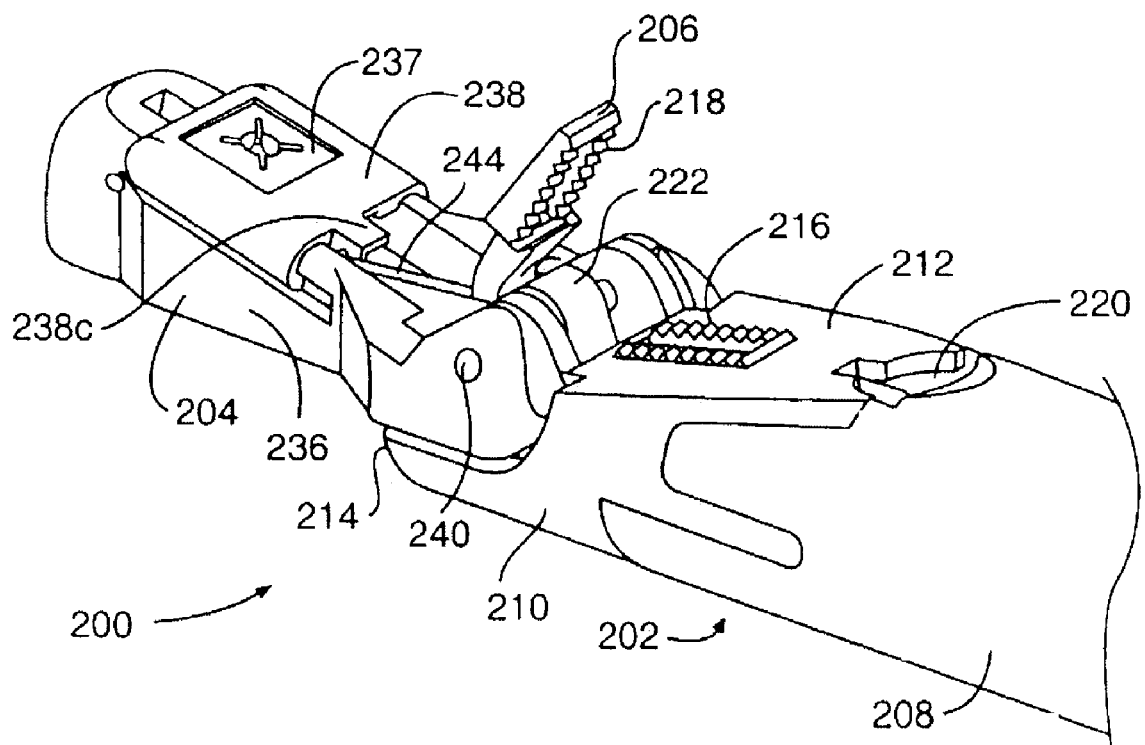
FIG. 26 is a perspective view of the presently preferred embodiment of the end effector in a second operative position.
Figure 27:
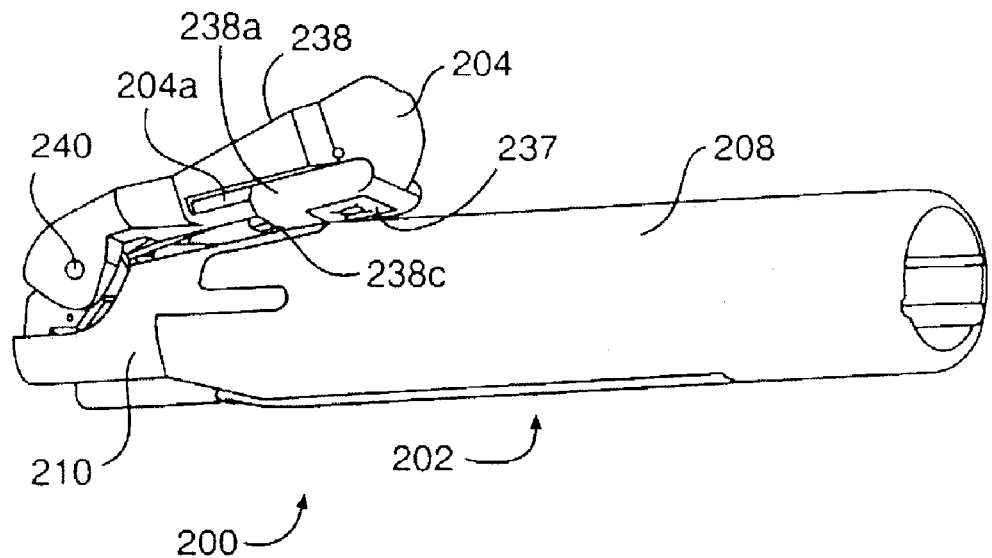
FIG. 27 is a perspective view of the presently preferred embodiment of the end effector in a third operative position.
Figure 31:
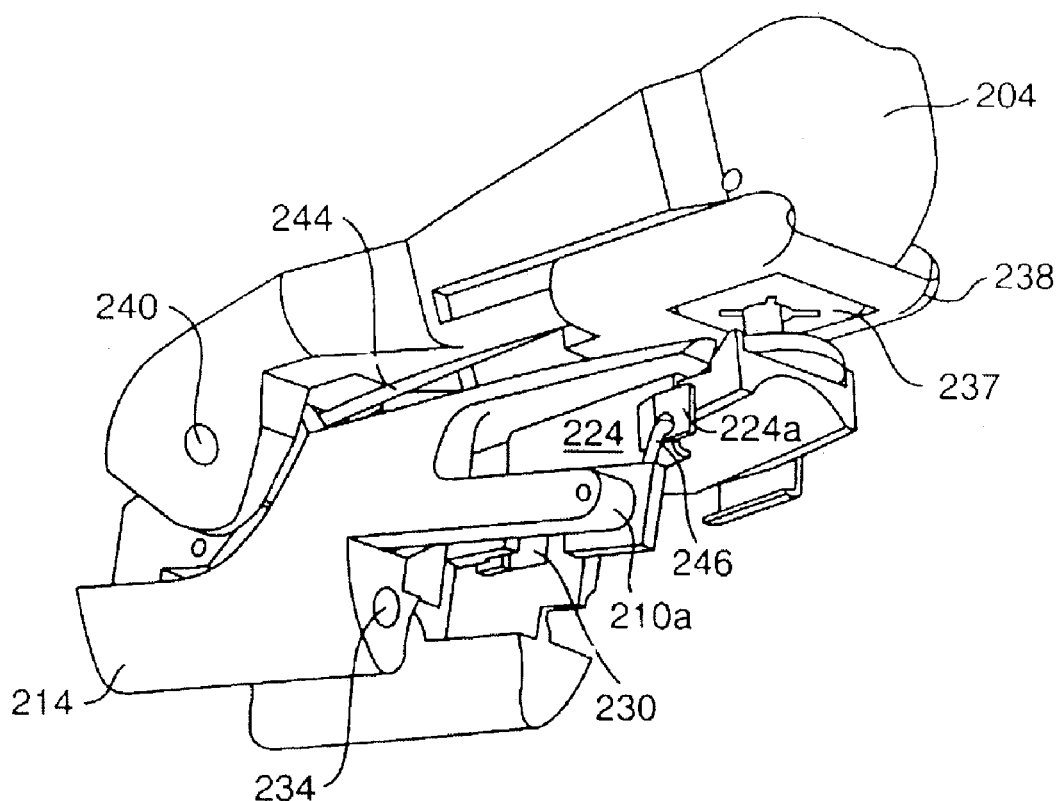
FIG. 31 is a perspective view of the major components of the presently preferred embodiment of the end effector in a fourth operative position.

FIG. 23 shows the lever 118 moved to the proximal position which pulls the cable 22 proximally and fires the male fastener part (as shown in FIG. 31). As seen best in FIG. 24, when the firing lever is in the proximal position, the stop 113 is located below the broad portion 118a. It will be appreciated that this position of the lever 118 will prevent the lever 136 from being moved distally. Distal movement of the lever 136 will attempt to rotate the cam 122 in a manner which will move the lever 118 in a direction where its broad portion 118a must pass the stop 113. Therefore, before the lever 136 can be moved to open the fastener head, the firing lever 118 must be moved back to the position shown in FIG. 22. As show in FIGS. 23 and 24, the lever 118 is preferably concave along its proximal side so that it can be moved over the lever 106.

Turning now to FIGS. 25–37, the presently preferred end effector and fasteners are similar to those described above with reference to FIGS. 1–10 with some differences which will become apparent from the following description.

Figure 28:
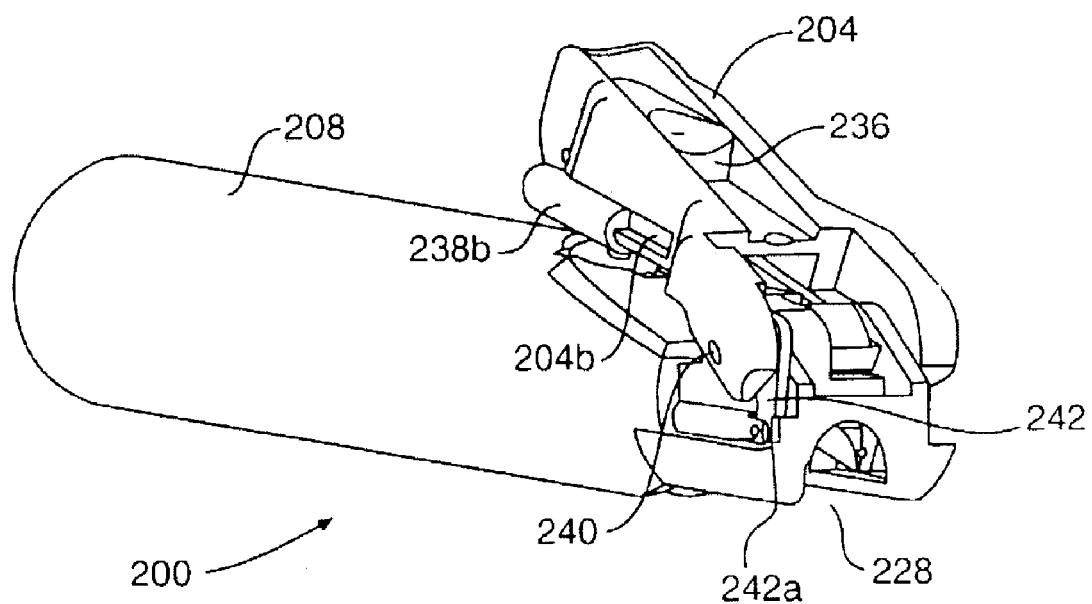
FIG. 28 is a perspective view of the distal end of the presently preferred embodiment of the end effector in the third operative position.
Figure 29:
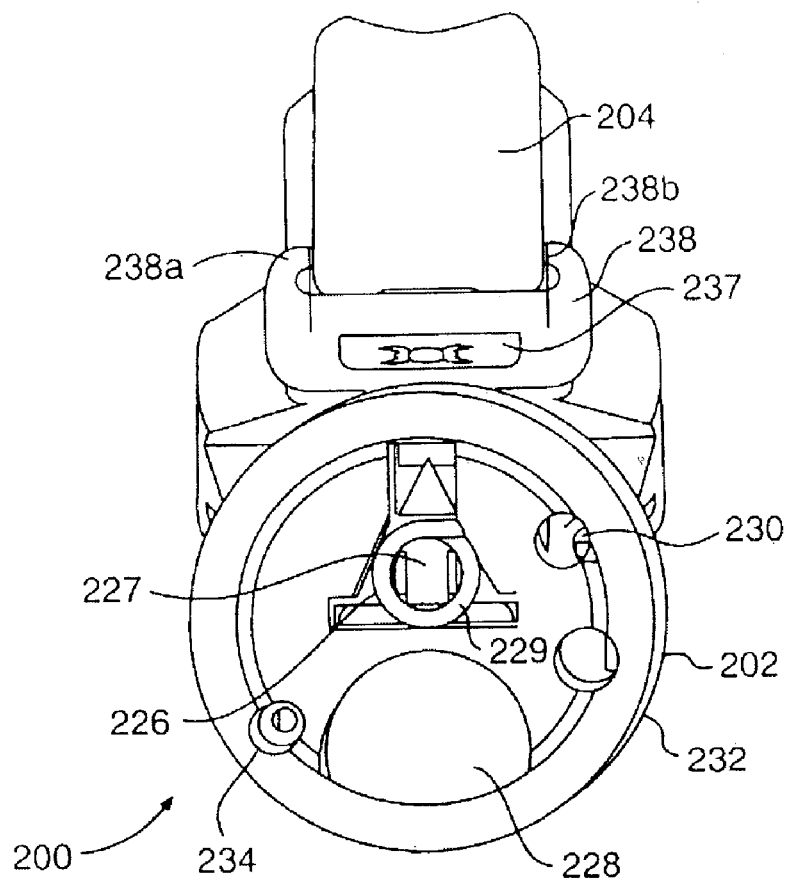
FIG. 29 is a perspective view of the proximal end of the presently preferred embodiment of the end effector in the third operative position.
Figure 30:
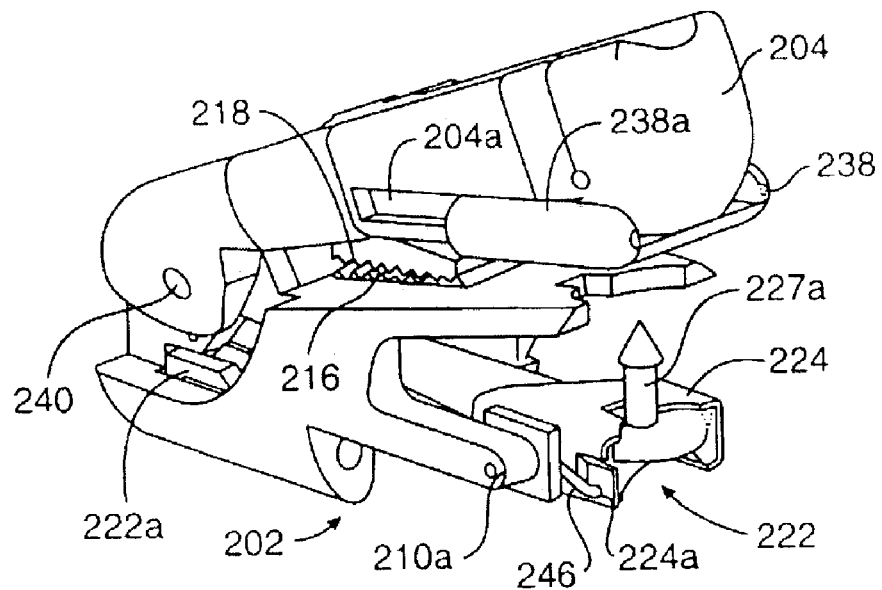
FIG. 30 is a perspective view of the major components of the presently preferred embodiment of the end effector in the third operative position.

The end effector 200 has a substantially cylindrical stationary member 202, a rotatable fastener head 204, and a grasper 206. The stationary member 202 has a relatively flexible proximal portion 208 and a relatively rigid distal portion 210. The distal portion 210 has a flattened part 212 which angles down toward the distal end 214 of the stationary member 202. The flattened part 212 is provided with a first grasping surface 216 and the grasper 206 is provided with a second grasping surface 218. A male fastener exit port 220 is located intermediate of the flattened part 212 and the proximal portion 208. As seen best in FIGS. 30 and 31, a firing member 222 with a movable male fastener part holder 224 is located inside the stationary member 202. As seen best in FIG. 29, a store 226 of male fastener parts 227 is located inside the stationary member 202, proximal of the firing member 222. Individual male fastener parts 227a are biased from the store into the male fastener part holder 224 by a spring 229 as shown in FIG. 30. According to this embodiment, up to six male fastener parts are held in the store. As seen best in FIGS. 28 and 29, an endoscope port 228 is provided in the stationary member 222 below the male fastener part store 226. Three cable ports 230, 232, 234 are provided in the stationary member 202 as shown in FIG. 29 for attaching control cables to the grasper 206, the fastener head 204, and the firing member 222, respectively.

The rotatable fastener head 204 includes a store 236 of female fastener parts 237 and a movable tray 238 for moving female fastener parts out of the store and into position to receive a male fastener part as described below. According to this embodiment, up to six female fastener parts are held in the store. The movable tray 238 is coupled to the fastener head 204 by flanges 238a, 238b which slideably engage grooves 204a, 204b in the fastener head as seen best in FIGS. 27–30. The movable fastener head 204 is coupled to the distal end 214 of the stationary member 202 by a pivot axle 240, and a hinged link 242 (FIG. 28) couples the fastener head 204 to a control cable (not shown). When the link 242 is moved distally, the fastener head 204 is moved to the closed position as shown in FIG. 28. When in this position, the hinge 242a in the link 242 is moved past the center of the pivot axle 240 which locks the fastener head in the closed position. The sliding tray 238 is coupled via a flange 238c and a pivoting link 244 to the pivot axle 240 as seen best in FIGS. 25 and 26. This link 244 causes the tray 238 to slide from the position shown in FIGS. 25 and 26 to the position shown in FIGS. 27 and 28 when the fastener head 204 is closed.

Figure 32:
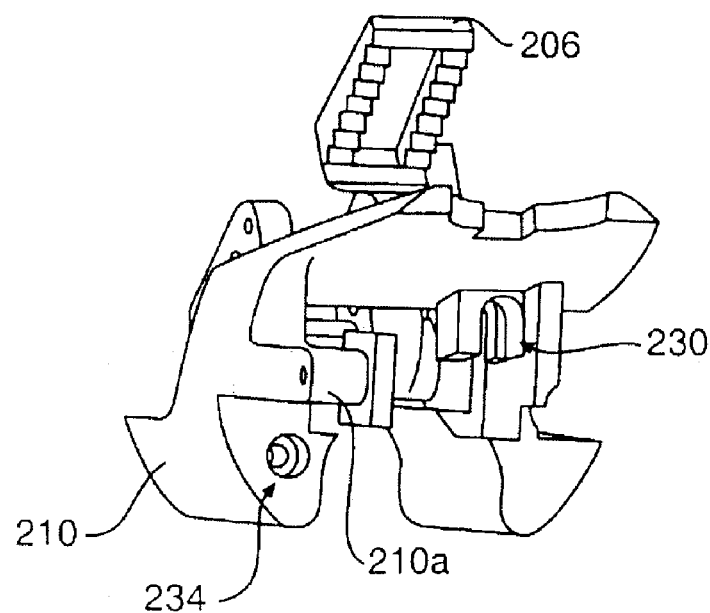
FIG. 32 is a perspective view of the stationary component and the grasper of the presently preferred embodiment of the end effector.
Figure 33:
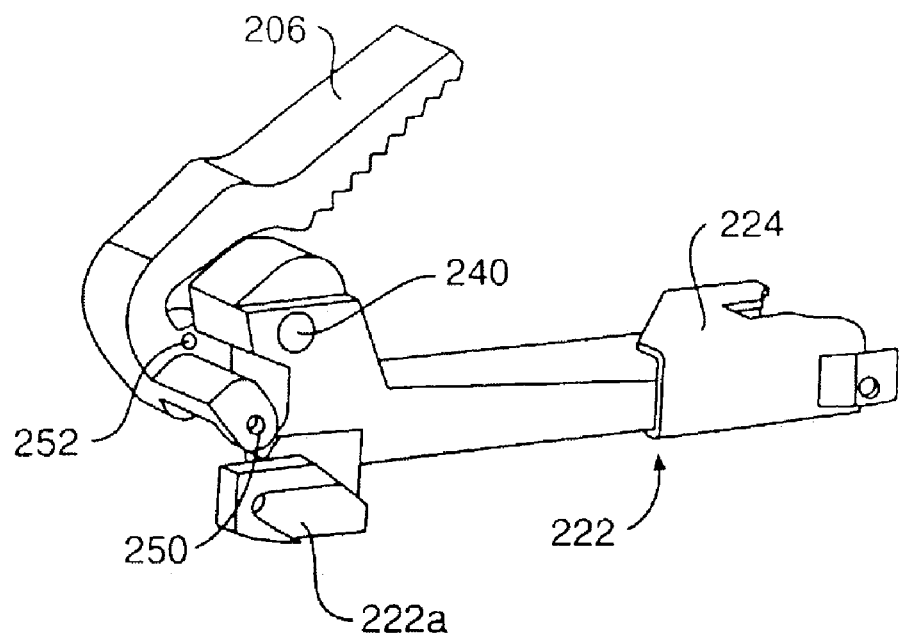
FIG. 33 is a perspective view of the grasper component and the fastener firing component of the presently preferred embodiment of the end effector.
Figure 34:
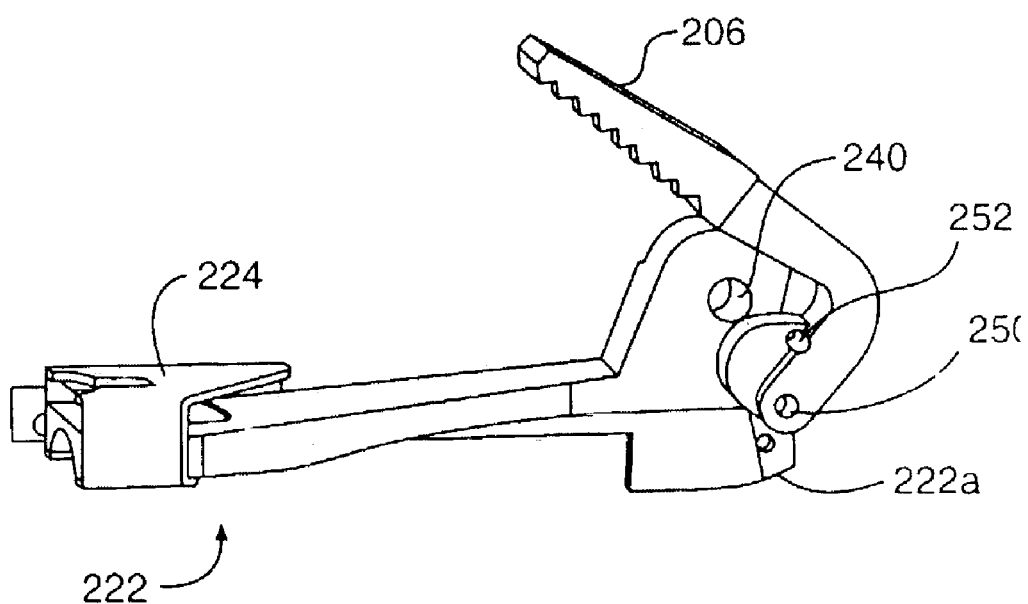
FIG. 34 is a view similar to FIG. 33 of the other side of the grasper component and the fastener firing component.

The firing member 222 is coupled to the stationary member 202 by the same pivot axle 240 as the fastener head as shown in FIGS. 25, 26, 30, 33, and 34. The firing member 222 is coupled to a control cable (not shown) by a lower flange 222a as shown in FIGS. 30, 33, and 34. As shown in FIG. 32, the distal portion 210 of the stationary member 202 is provided with a stepped port 234 through which the control cable for the firing member passes and which holds the cable sheath. When the control cable pulls the flange 222a proximally, the firing member 222 is moved towards the exit port 220. The movable male fastener part holder 224 is provided with a proximal flange 224a which is coupled to a lateral portion 210a of the stationary member 202 by a pivoting link 246 as seen best in FIG. 30. This link 246 causes the holder 224 to slide distally as shown in FIG. 31 when a male fastener part is fired. The purpose of the holder 224 is to prevent the male fastener part from falling out through the port 220 when the fastener head is open and to allow the firing operation to be aborted while retaining the male fastener part.

As seen best in FIGS. 33 and 34, the grasper 206 is pivotally coupled to the distal end of the firing member 222 on a pivot axle 250. The grasper 206 is also coupled to a control cable (not shown) via a hole 252 located above its pivot connection. As shown in FIGS. 31 and 32, the distal portion 210 of the stationary member 202 is provided with a stepped port 230 through which the control cable for the grasper passes and which holds the cable sheath. When the control cable is pulled proximally, the grasper is moved to the closed position shown in FIG. 25.

Figure 35:
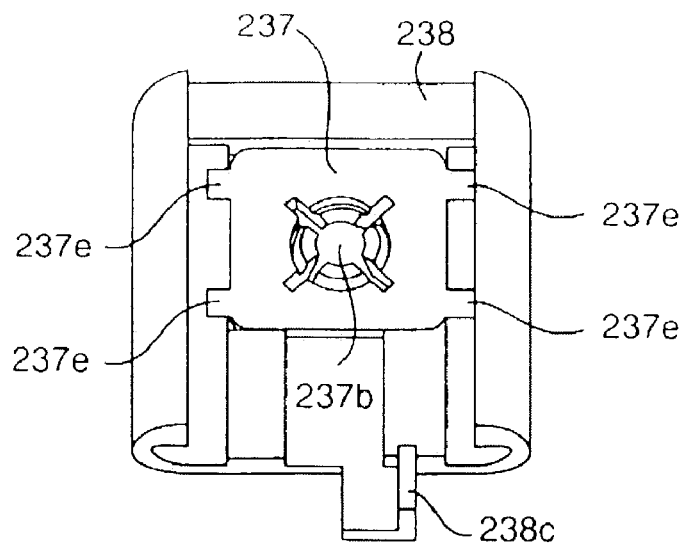
FIG. 35 is a perspective view of the top side of a presently preferred embodiment of a female fastener part in the female fastener carrier.
Figure 36:
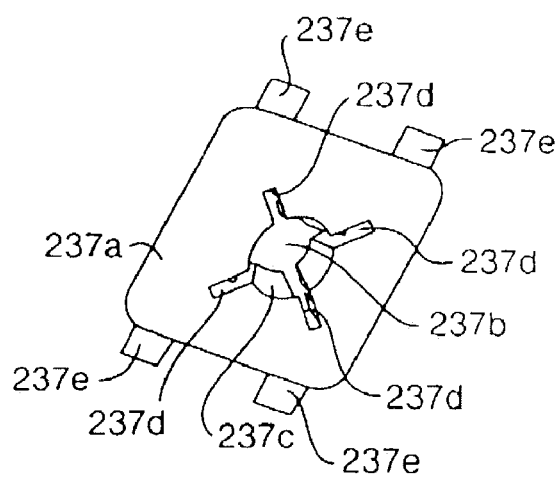
FIG. 36 is a perspective view of the bottom of the presently preferred female fastener part.
Figure 37:
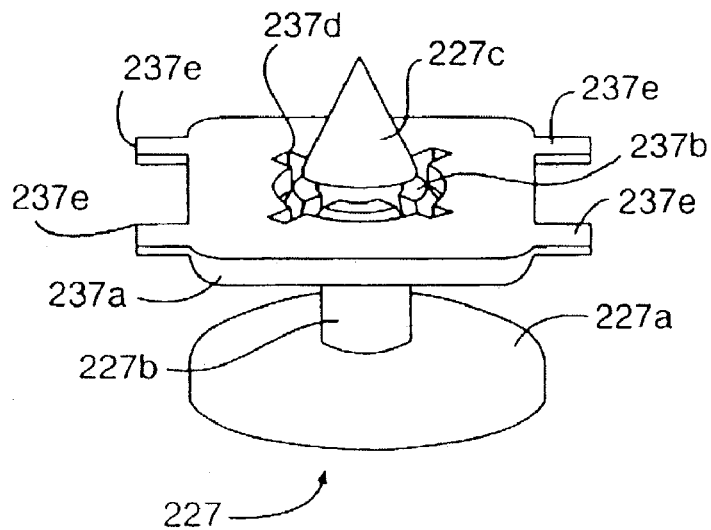
FIG. 37 is a perspective view of the presently preferred female fastener part coupled to the male fastener part.

Turning now to FIGS. 35–37, the presently preferred male fastener part 227 (substantially the same as the fastener part 46 described above) has a disk shaped base 227a, a central upstanding shaft 227b, and tapered barb 227c at the end of the shaft. The presently preferred female fastening member 237 is a substantially flat rectangular member 237a defining a central hole 237b. The hole 237b has a tapered entry 237c and four radial strain relief slots 237d. Four flexible or frangible peripheral tabs 237e are provided on the periphery of the rectangular member. These tabs hold the fastener part in the tray 238 as shown in FIG. 35, but allow it to be pulled out of the tray after it is coupled to a male fastener part as shown in FIG. 37.

Turning now to FIGS. 38–48, an alternate preferred end effector 300 is similar to the end effector 200 described above, with similar reference numerals referring to similar parts.

The end effector 300 has a substantially cylindrical stationary member 302, a rotatable fastener head 304, and a grasper 306. The stationary member 302 has a flattened part 312 which angles down toward the distal end 314 of the stationary member 302. The flattened part 312 is provided with a first grasping surface 316 and the grasper 306 is provided with a second grasping surface 318. A male fastener exit port 320 is located at the proximal end of the flattened part 312. As seen best in FIGS. 38–44, a firing member 322 with a male fastener part holder 324 is located inside the stationary member 302.

Figure 43:
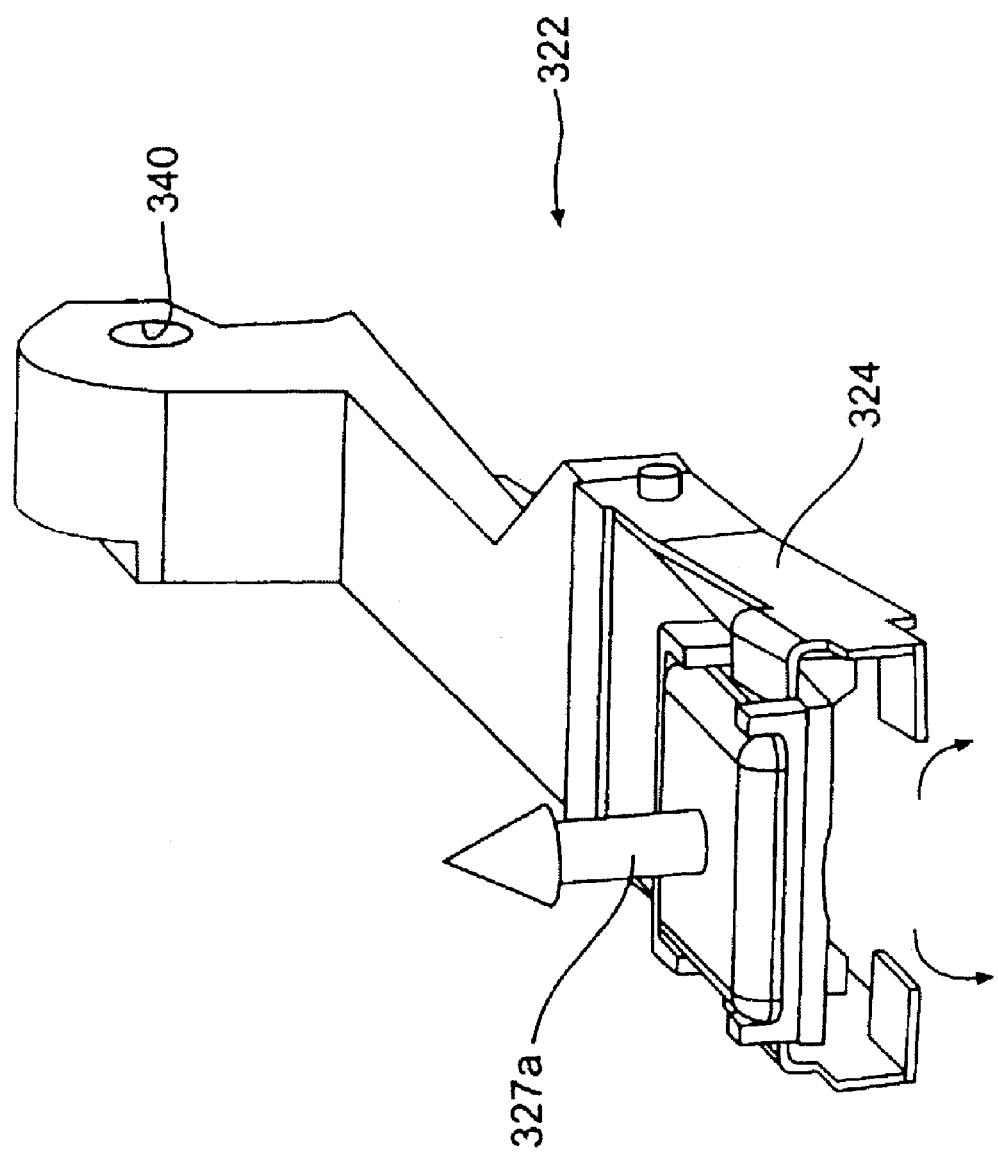
FIG. 43 is a perspective view of the firing member with the leaf spring disengaged from the male fastener part to release the male fastener part.
Figure 44:
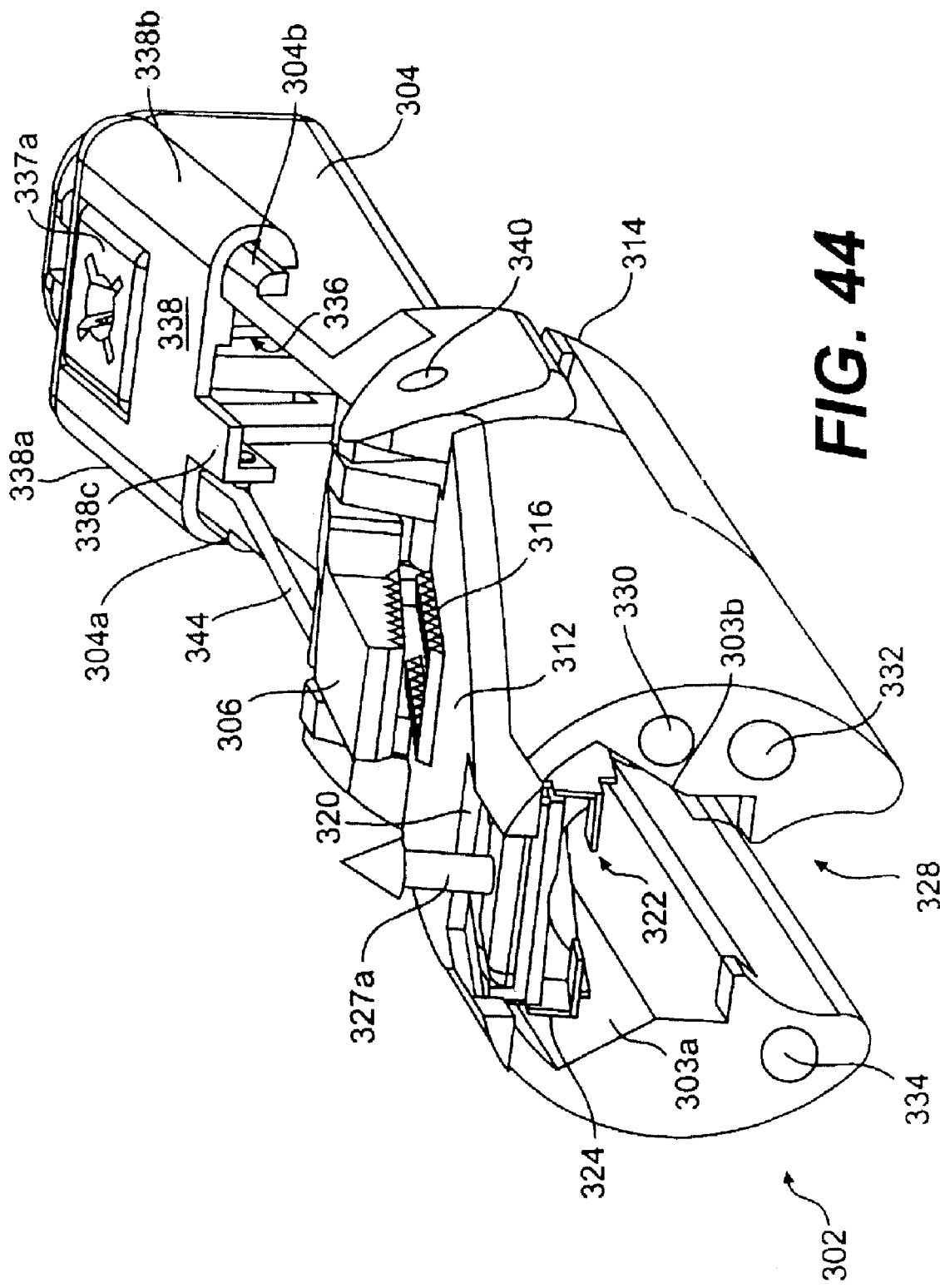
FIG. 44 is a perspective view showing the end effector with the firing member with a male fastener part with the leaf spring disengaged from the male fastener part to release the male fastener part.
Figure 45:
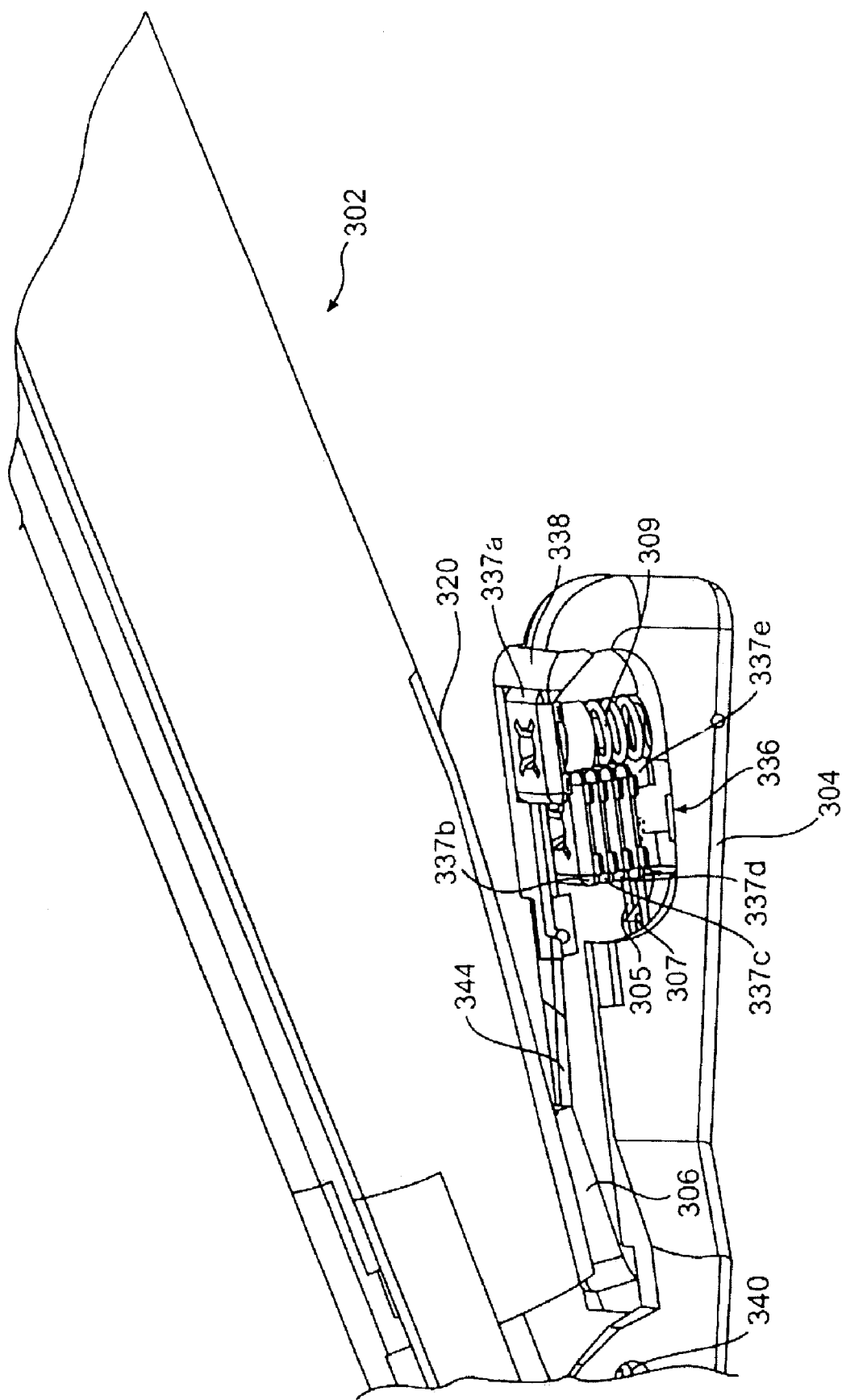
FIG. 45 is a broken, partially cut away perspective view of the embodiment of FIGS. 38–44 showing the store of female fastener parts with a female fastener part in position to receive a male fastener part.

As seen best in FIGS. 41–44, the holder 324 has a pair of flanged springy arms 324a, 324b which hold the base of a male fastener part, e.g. 327a. The arms 324a, 324b are biased outward to the position shown in FIG. 43. As seen best in FIGS. 41 and 44, the interior of the stationary member 302 has contoured walls 303a, 303b which hold the arms 324a, 2324b close together, securing the male fastener part. When the firing member 322 is raised into the firing position, as shown in FIGS. 40 and 44, the springy arms 324a, 324b move outward as shown in FIG. 43, thereby releasing the male fastener part.

Figure 38:
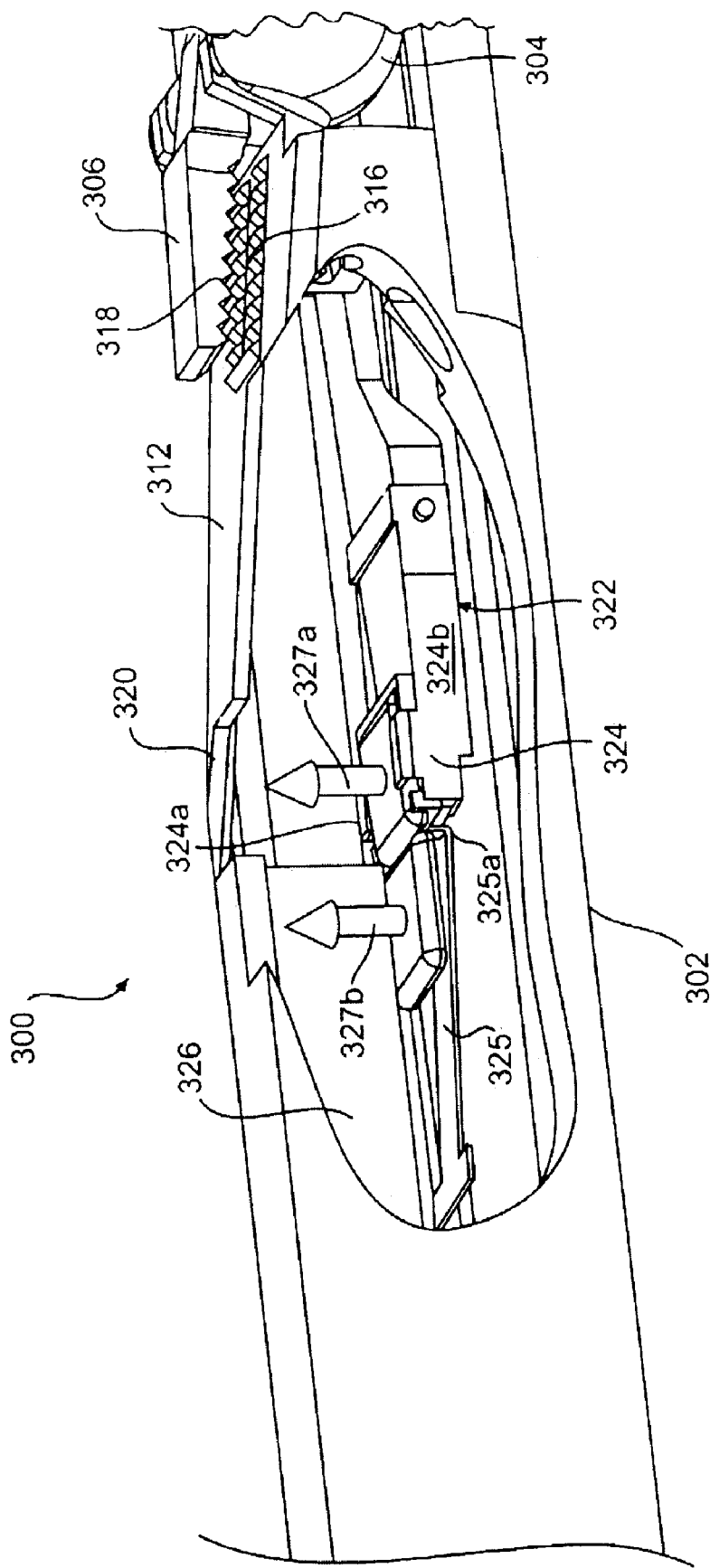
FIG. 38 is a broken, partially cut away perspective view of an alternate preferred embodiment showing the firing member receiving a male fastener part.
Figure 39:
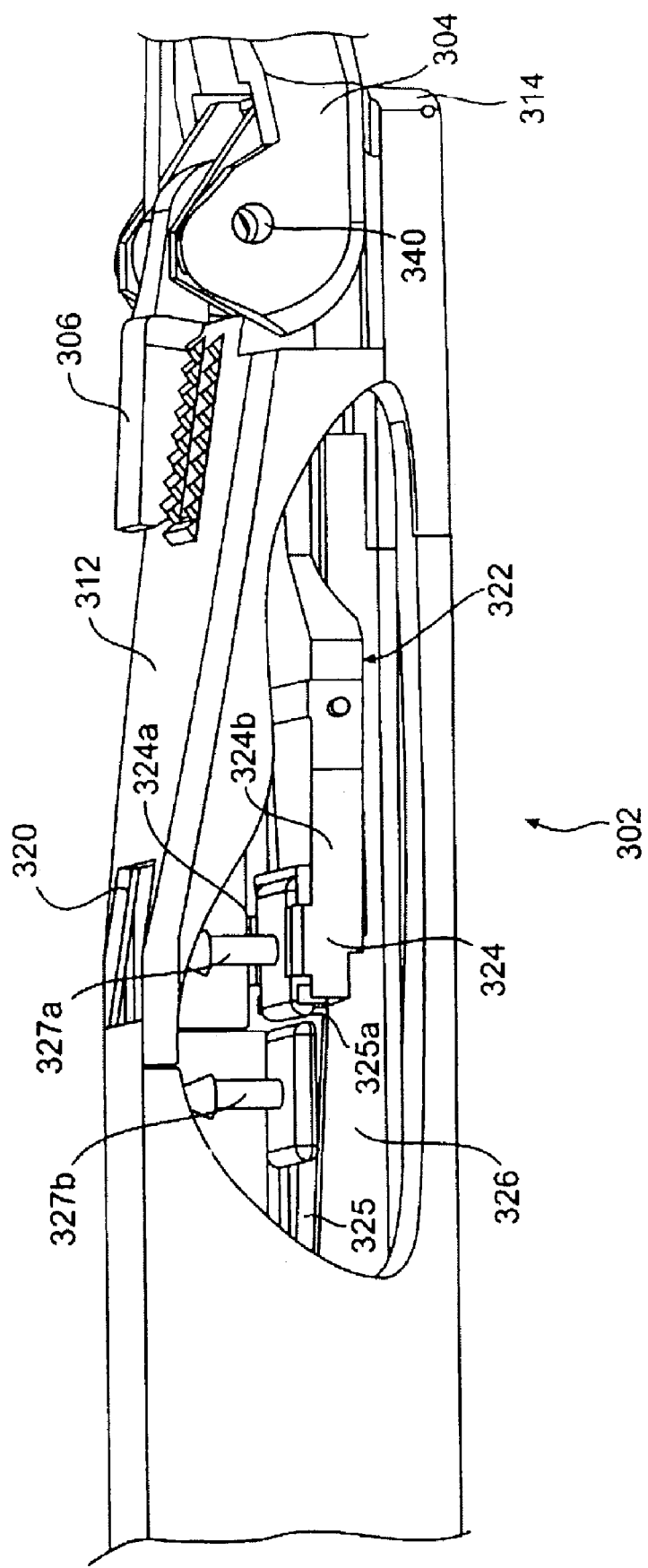
FIG. 39 is a view similar to FIG. 38 from a different perspective.
Figure 40:
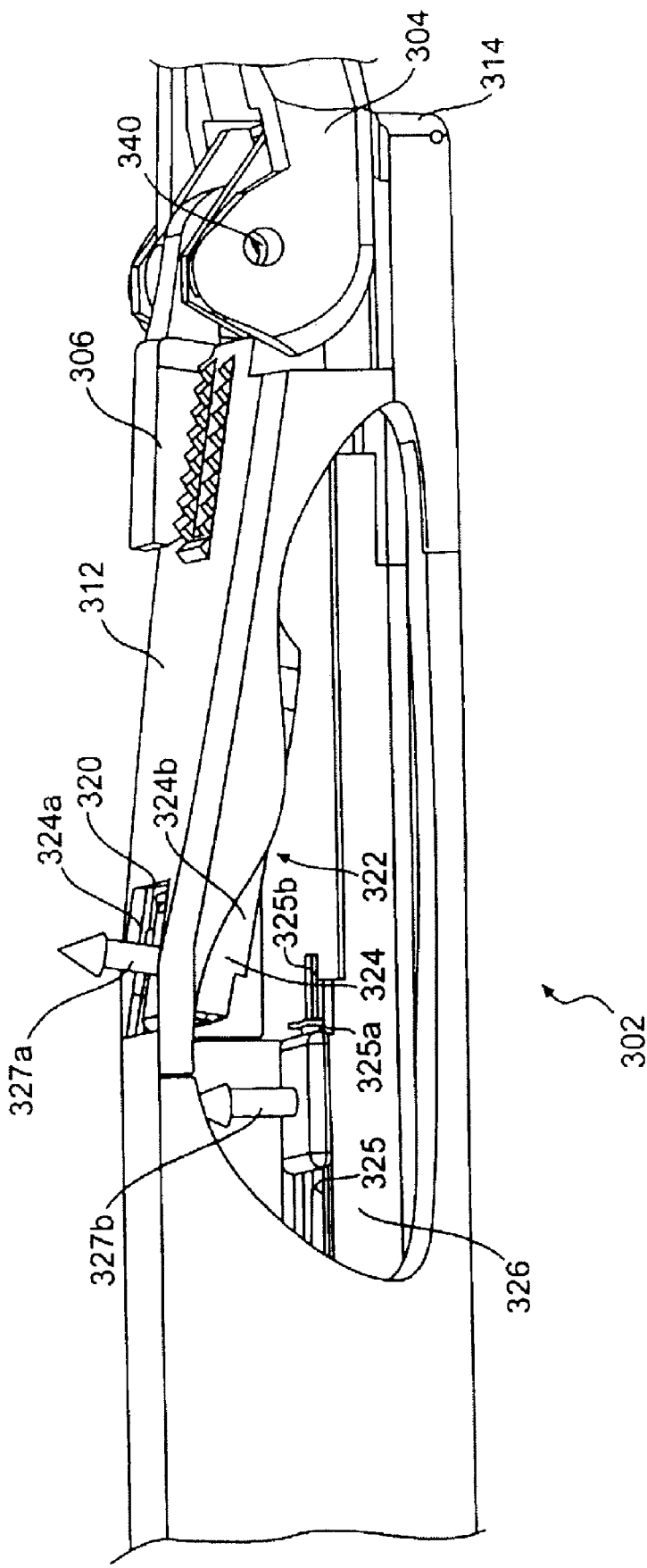
FIG. 40 is a view similar FIG. 39 showing the firing member raised and the leaf preventing a male fastener part from moving off the track.

As seen best in FIGS. 38–40, a store 326 of male fastener parts 327a, 327b, etc. is located inside the stationary member 302, proximal of the firing member 322. Individual male fastener parts 327a, 327b, etc. are biased from the store into the male fastener part holder 324 by a spring (not shown). According to this embodiment, a leaf spring 325 having an upstanding flange 325a and a distal tongue 325b (FIG. 40) is arranged beneath the row of male fastener parts in the store 326. As shown in FIG. 40, the distal most fastener part is prevented from exiting the store 326 by the flange 325a when the firing member 322 is in the firing position. When the firing member 322 returns from the firing position as seen in FIGS. 38 and 39, the tongue 325b of the leaf spring is depressed by the firing member 322 and the flange 325a is thereby moved away from the next fastener part allowing it to enter the holder 324 of the firing member 322.

Figure 41:
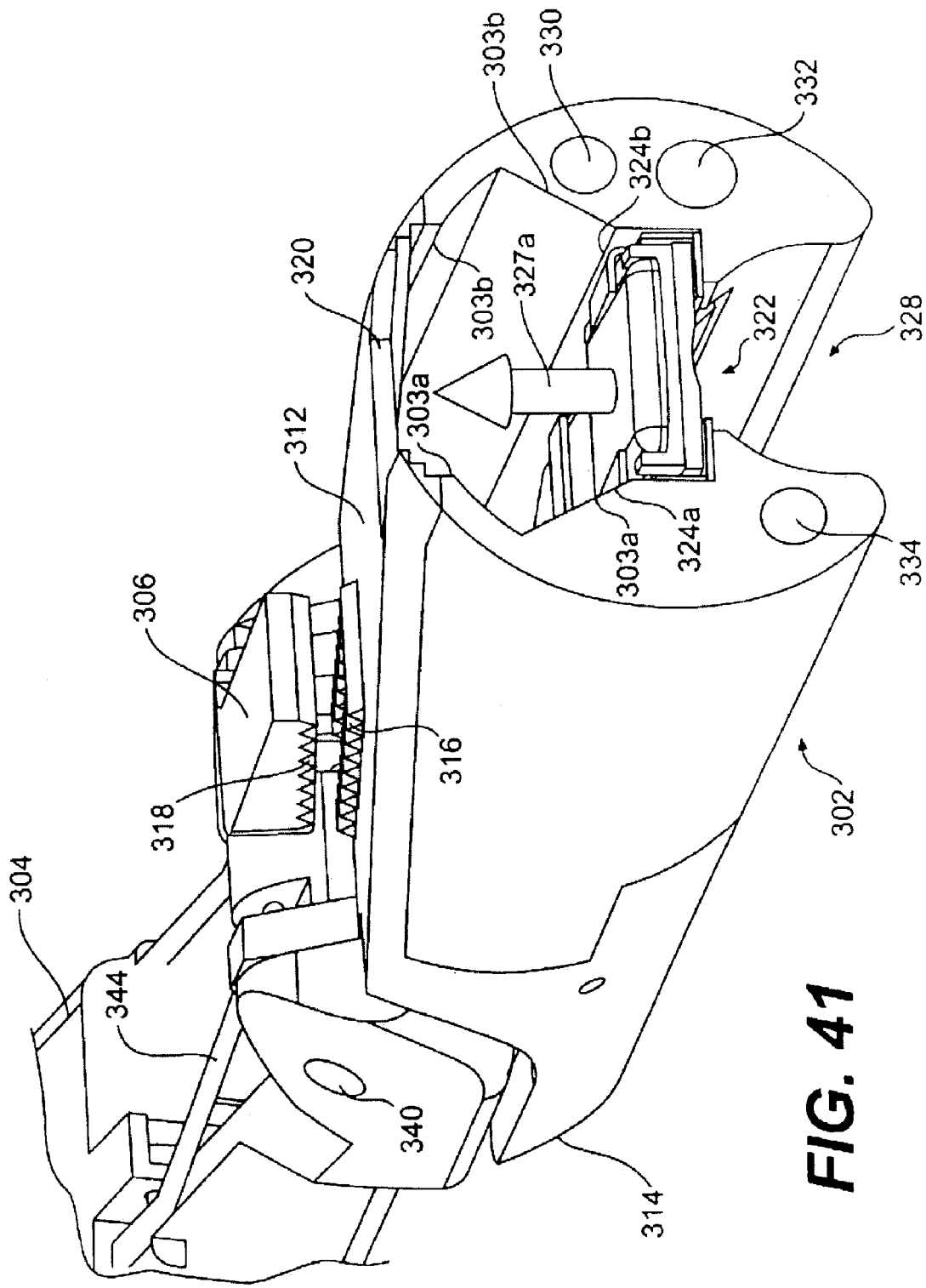
FIG. 41 is a broken perspective view of the embodiment of FIGS. 38–40 showing the end effector with the firing member with a male fastener part engaged therein.
Figure 42:
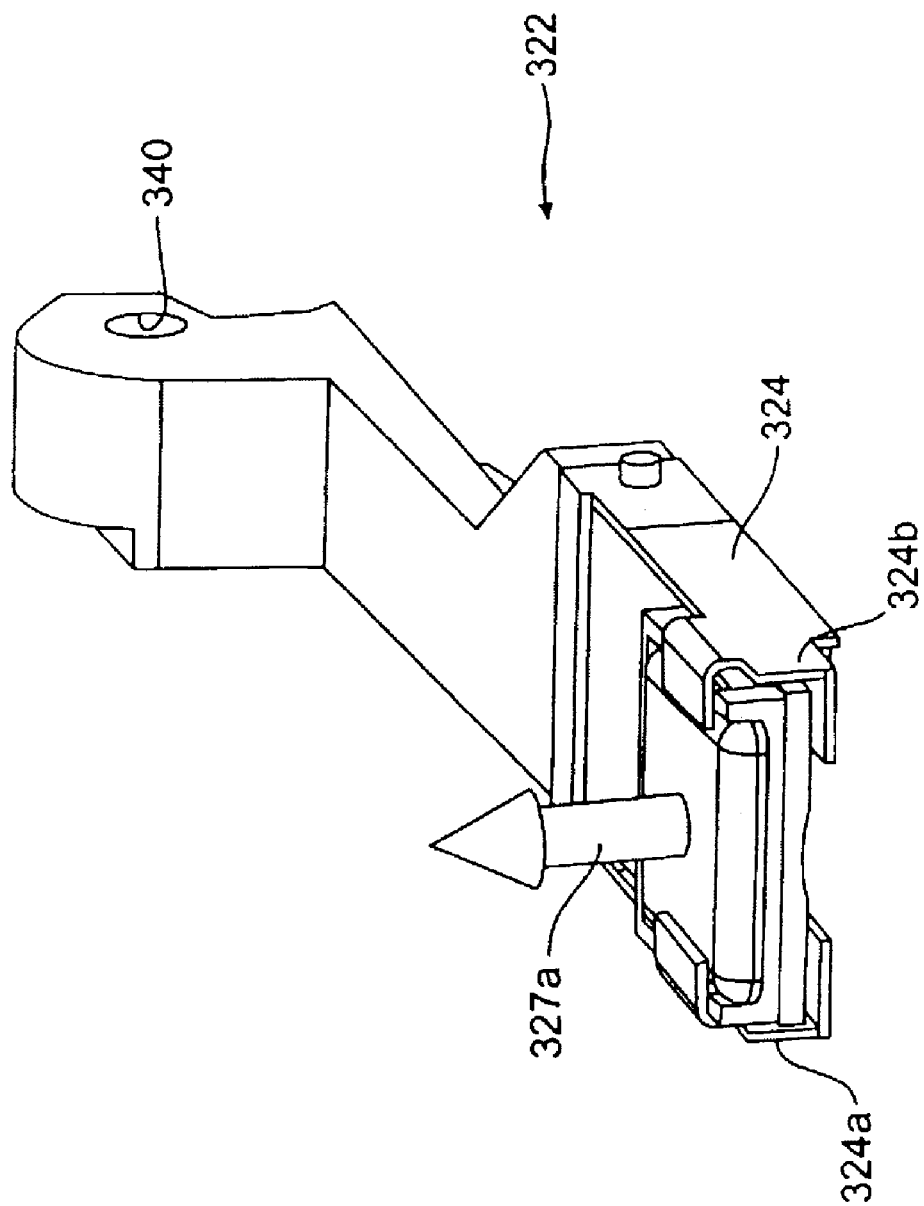
FIG. 42 is a perspective view of the firing member and male fastener part engaged therein by a leaf spring.

As seen best in FIGS. 41, 44, and 48, an endoscope port 328 is provided in the stationary member 322 below the male fastener part store 326. Three cable ports 330, 332, 334 are provided in the stationary member 302 as shown in FIGS. 41 and 44 for attaching control cables to the grasper 306, the fastener head 304, and the firing member 322, respectively.

As shown in FIGS. 41–48, the rotatable fastener head 304 includes a store 236 of female fastener parts 337 and a movable tray 338 for moving female fastener parts out of the store and into position to receive a male fastener part as described below. According to this embodiment, up to six female fastener parts are held in the store. As seen best in FIG. 44, the movable tray 338 is coupled to the fastener head 304 by flanges 338a, 338b which slideably engage flanges 304a, 304b in the fastener head. The sliding tray 338 is coupled via a flange 338c and a pivoting link 344 to the pivot axle 340 as seen best in FIGS. 44, 45, and 48. This link 344 causes the tray 338 to slide from the position shown in FIG. 44 to the position shown in FIGS. 45 and 48 when the fastener head 304 is closed.

Figure 46:
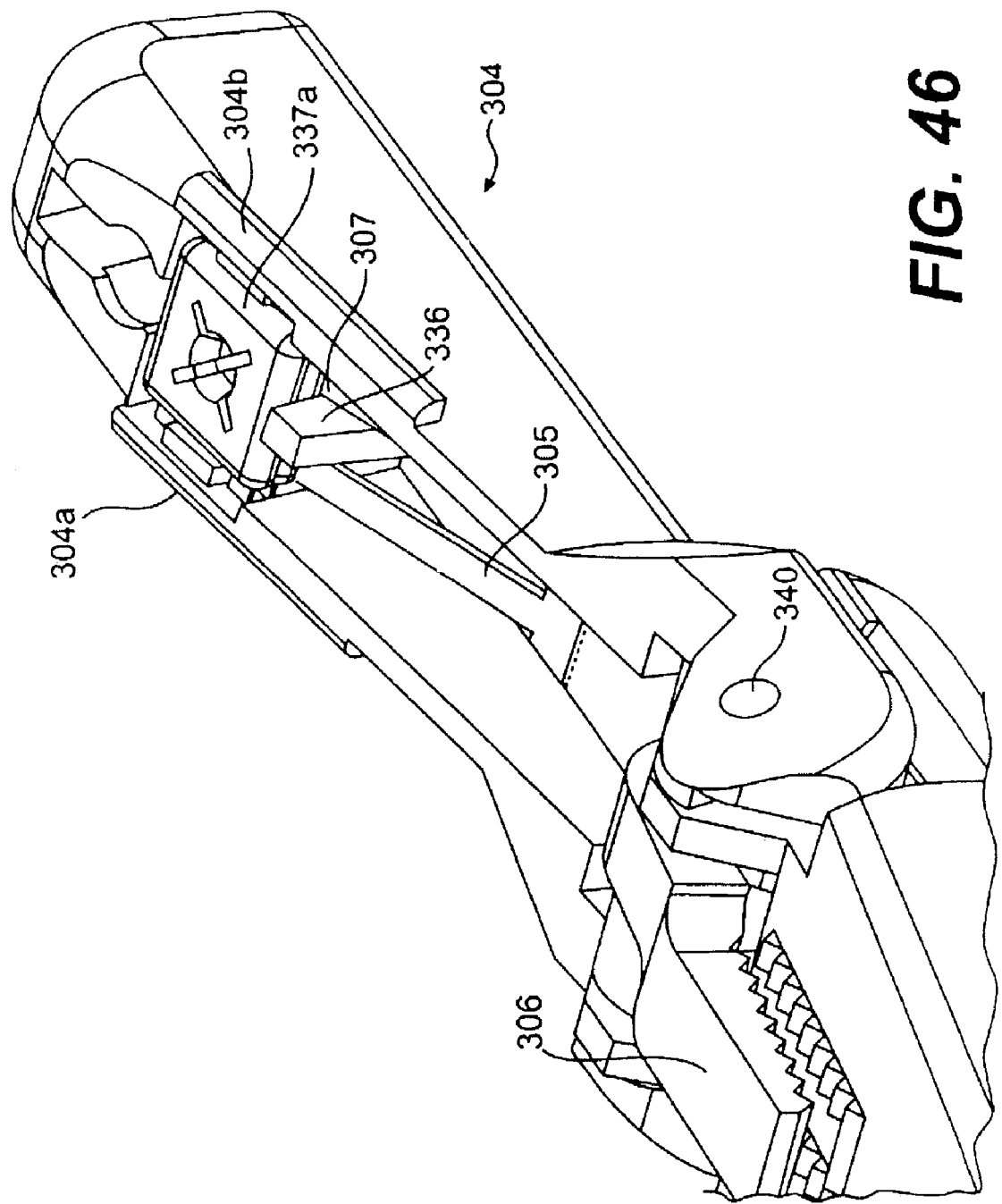
FIG. 46 is a broken perspective view of the embodiment of FIGS. 38–45 showing the female fastener part shuttle in position to retrieve a female fastener part from the store of female fastener parts.
Figure 47:
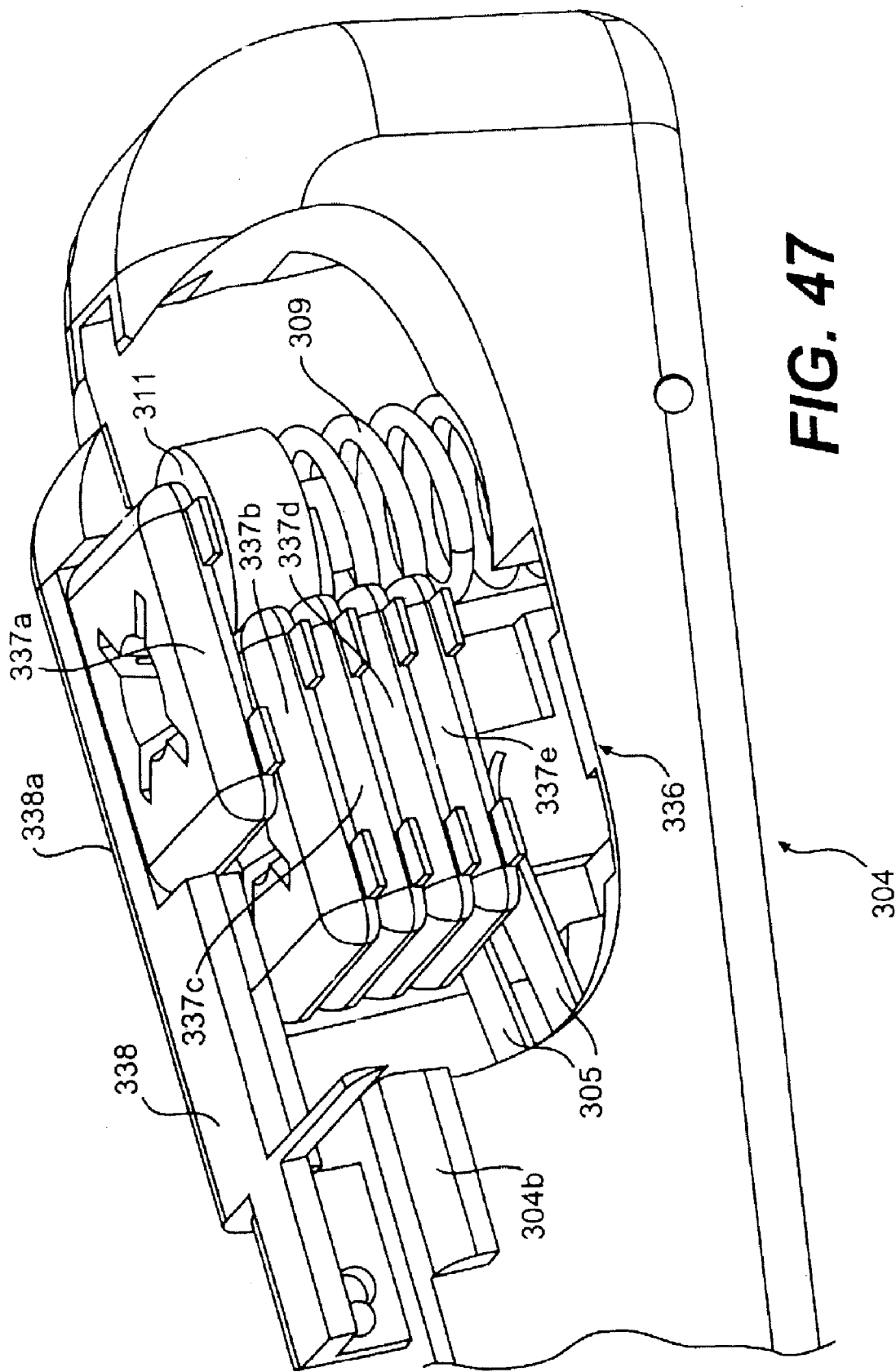
FIG. 47 is a broken, partially cut away perspective view of the embodiment of FIGS. 38–46 showing the female fastener part shuttle in an intermediate position.
Figure 48:
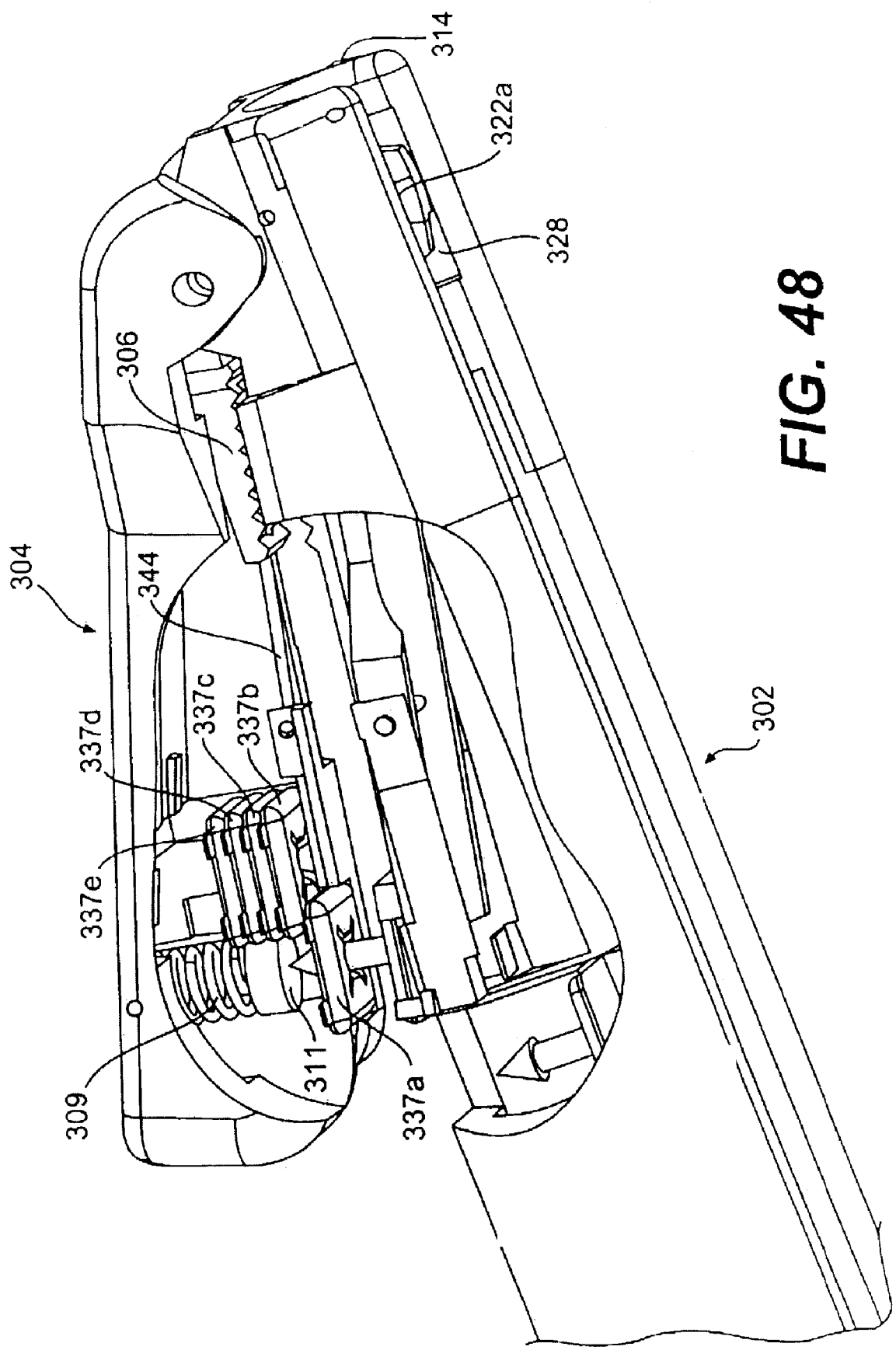
FIG. 48 is a broken, partially cut away perspective view of the embodiment of FIGS. 38–47 showing the female fastener part and male fastener parts coupled with the ejector spring engaging the barb of the male fastener part.

As seen best in FIGS. 45–48, the female fastener parts 337a–337e are biased out of the store 336 by a bifurcated leaf spring 305 and are held laterally in line by a support post 307 which is seen best in FIG. 46 where the movable tray has been removed to better expose the spring 305 and the post 307. A fastener discharge spring 309 is located adjacent to the female fastener store 336 and is provided with a male fastener engaging surface 311. As the fastener head 304 is moved from the open position shown in FIG. 46 to the closed position shown in FIG. 45, the movable tray 338 moves the top most female fastener part 337a out of the store and over the discharge spring 309. FIG. 47 shows the tray 338 in a midway position as the fastener 337a is being moved into position to receive a male fastener part. When a male fastener is fired into the female fastener as shown in FIG. 48, The end of the male fastener will engage the surface 311 on the spring 309 and compress the spring. It will be appreciated that as the firing member 322 is returned from the firing position, the spring 309 will push against the end of the male fastener thereby pushing the female fastener out of the tray, bending or breaking the tabs of the female fastener.

The firing member 322 is coupled to the stationary member 302 by the same pivot axle 340 as the fastener head as shown in FIGS. 39, 40, 42, 43 and 48. The firing member 322 is coupled to a control cable (not shown) by a lower flange 322a as shown in FIG. 48. When the control cable pulls the flange 322a proximally, the firing member 322 is moved towards the exit port 320.

Figure 49:
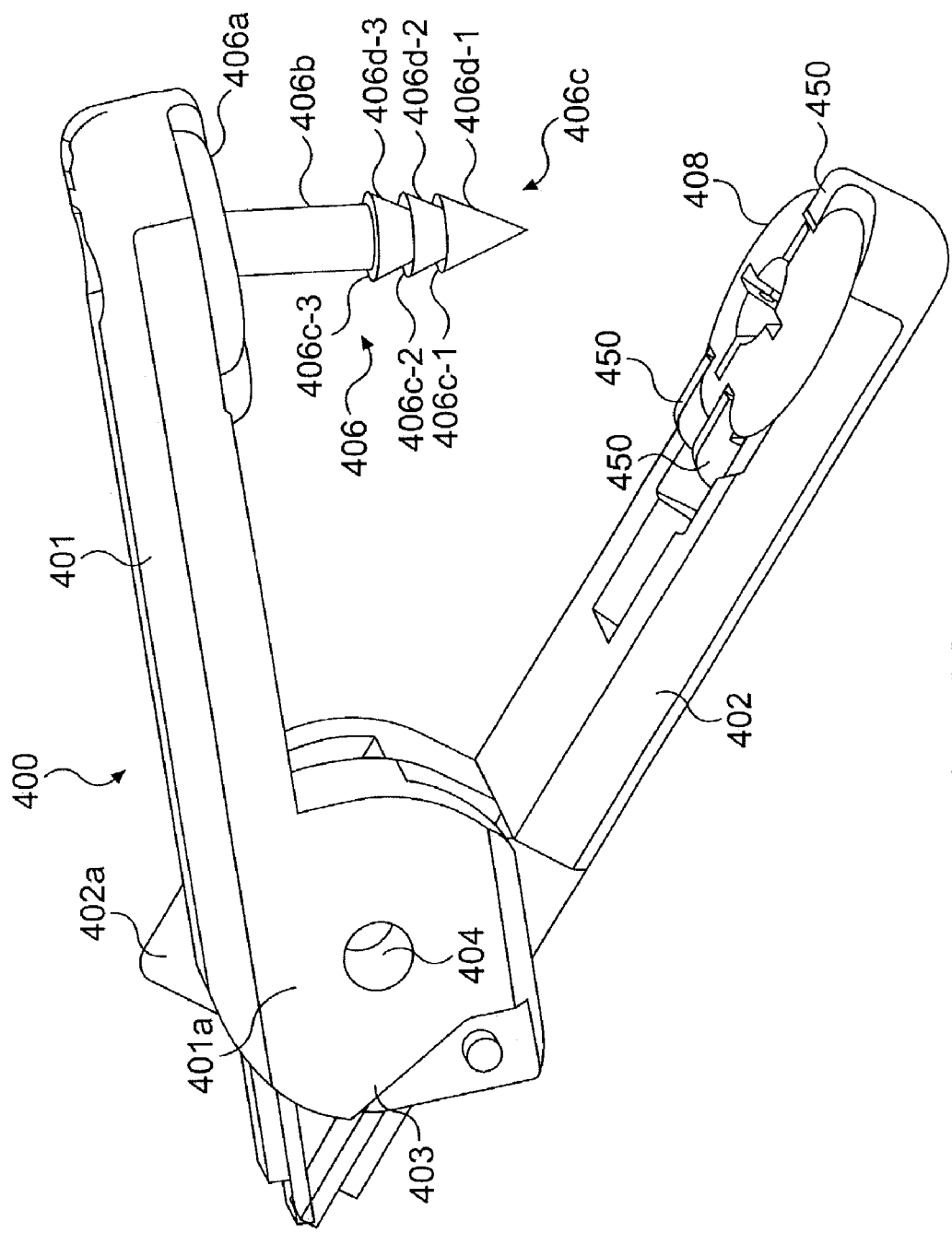
FIG. 49 is a perspective view of an end effector according to an embodiment of the present invention showing male and female fastener parts in position on the end effector.
Figure 50:
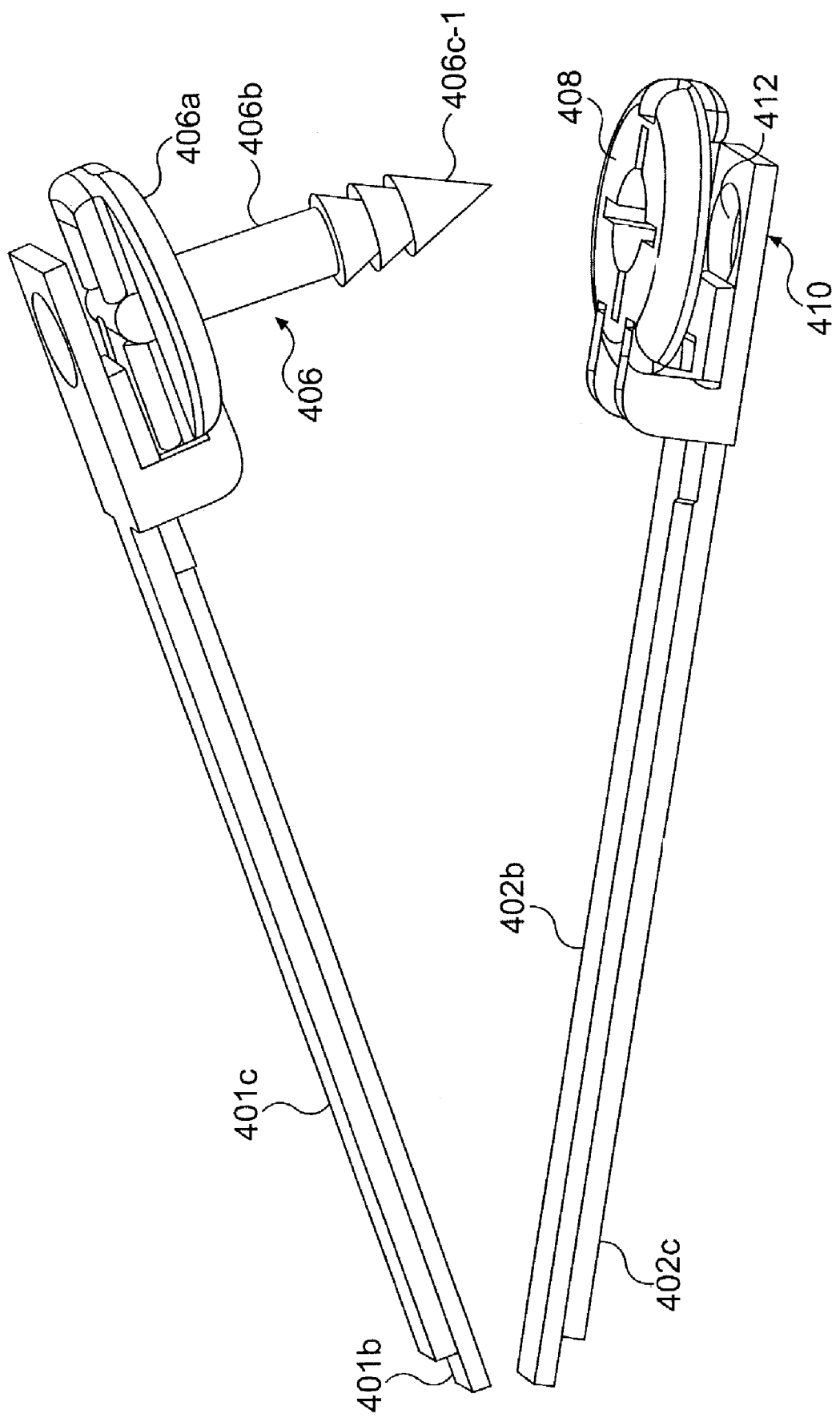
FIG. 50 is a perspective view of portions of the internal frame of the end effector of FIG. 49, showing a shearing mechanism in relation to the female fastener part.
Figure 51:
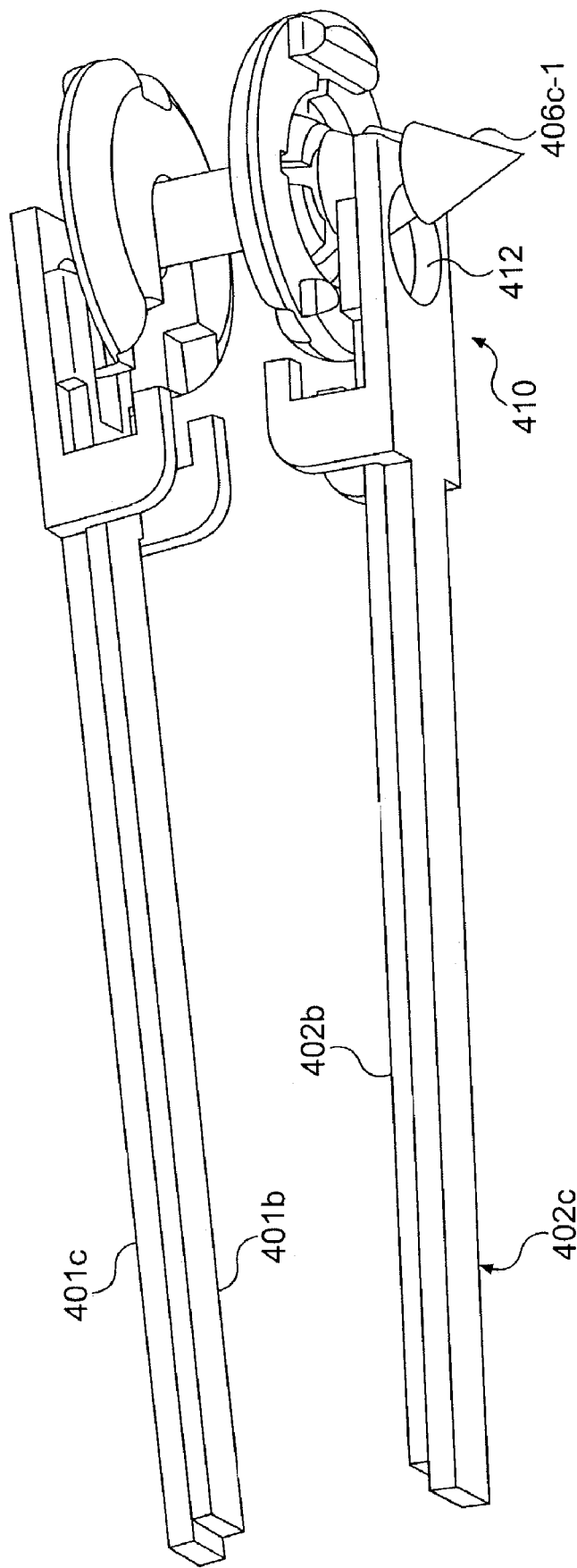
FIG. 51 is a perspective view of portions of the internal frame of the end effector of FIG. 49, showing the shearing mechanism severing the tip of the male fastener part as the fastened connector is ejected from the end effector.

FIGS. 49–51 show an end effector 400 of a surgical instrument according to another embodiment of the present invention. End effector 400 includes a first actuator arm 401 pivotally connected to a second actuator arm 402 by a suitable pivoting mechanism 403. Pivoting mechanism 403 can include a pivot pin (not shown) that extends through an aperture 404 extending through proximal ends 401a, 402a of actuator arms 401, 402, respectively. End effector 400 also may be used in combination with aspects of the various embodiments of surgical instruments described above. For example, end effector 400 may include a grasping mechanism, such as those described in connection with end effectors described above or may be used in an endoscopic procedure in combination with a separate grasping instrument. End effector 400 also may connect to a distal end of an elongate tube, such as a distal end of the elongate, flexible tubes described above, in any suitable manner known in the art. End effector 400 also may be operated by a proximal actuator that is coupled to end effector 400 by a suitable control mechanism such as those described above.

End effector 400 is configured to hold a male fastener 406, as shown positioned on actuator arm 401. Male fastener 406 has a base 406a, a shaft 406b, and a tip 406c. The tip 406c is provided with multiple detent positions 406c-1, 406c-2, and 406c-3 defined by barbs 406d-1, 406d-2, and 406d-3. The male fastener depicted herein has three such barbs, but any number of barbs and corresponding detent positions could be provided as required by, for example, the thickness of tissue to be fastened together and the procedure to be performed.

Figure 53:
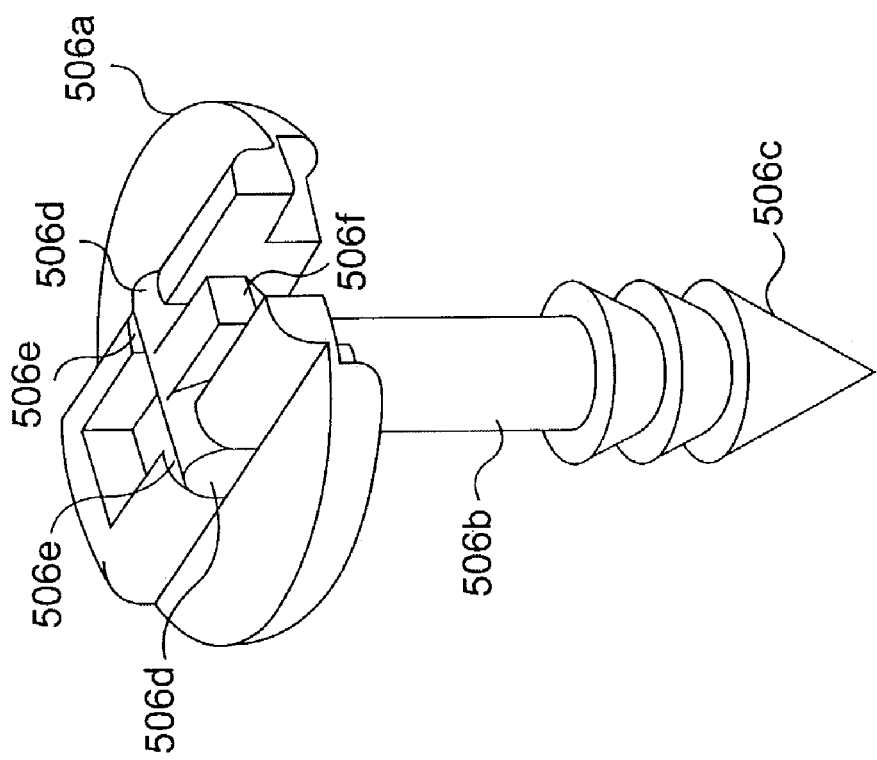
FIGS. 52 and 53 are perspective views of a hinged male fastener part according to an embodiment of the present invention.
Figure 52:
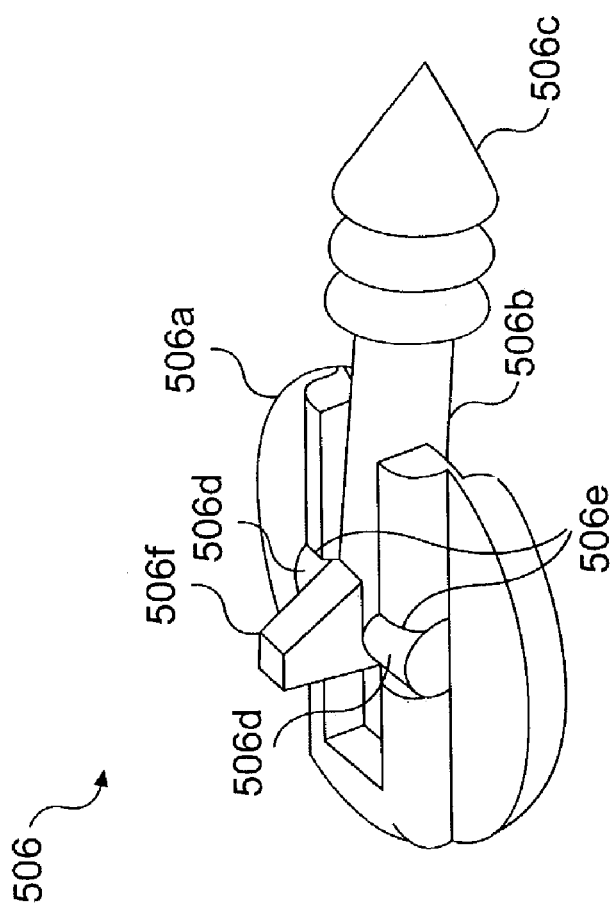

FIGS. 52 and 53 show an alternative configuration of a male fastener 506 to be used with end effector 400. Here, male fastener 506 is provided with a base 506a and a shaft 506b that has a tip 506c, similar to that depicted in FIGS. 49–51. At the base of shaft 506b are provided rounded tabs 506d that fit into slots 506e formed into base 506a. Tabs 506d resting in slots 506e permit shaft 506b to rotate in a hinge-like fashion from a retracted position (FIG. 52) to a deployed position (FIG. 53). The ability of shaft 506b to attain a retracted position lying in substantially the same plane as that of base 506a allows the male fastener assembly to be more easily stored in a smaller space within the surgical instrument. This flat storage configuration can allow for storage of a larger number of male fasteners and/or use of a smaller size end effector, reducing trauma to the patient. This configuration also allows for a longer shaft than could be used with a non-retractable fastener. In addition, a deployment tab 506f may be provided at the base of shaft 506b. In operation, as male fastener 506 is moved into position at the distal end of effector arm 401, tab 506f would come into contact with a surface on arm 401 that would then apply force to tab 506f, causing shaft 506b to rotate into a deployed position. Once deployed, male fastener 506 would then operate in a similar same fashion as a non-retractable male fastener, such as those described above.

Figure 58:
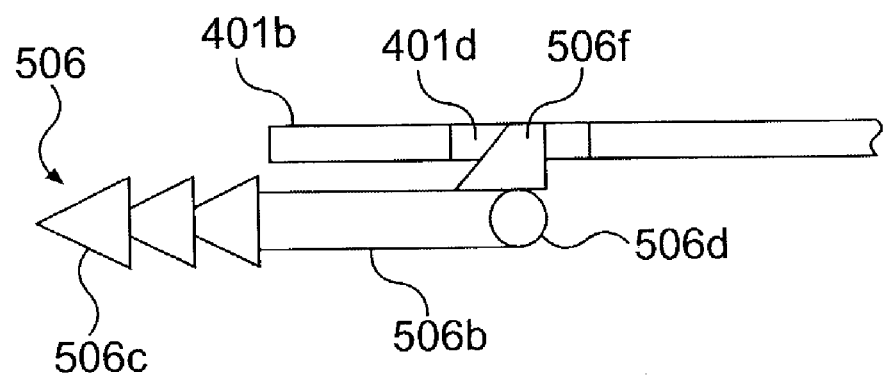
FIGS. 58 and 59 are side elevations of the male fastener part showing how the end effector arm causes the shaft to rotate into position.
Figure 59:
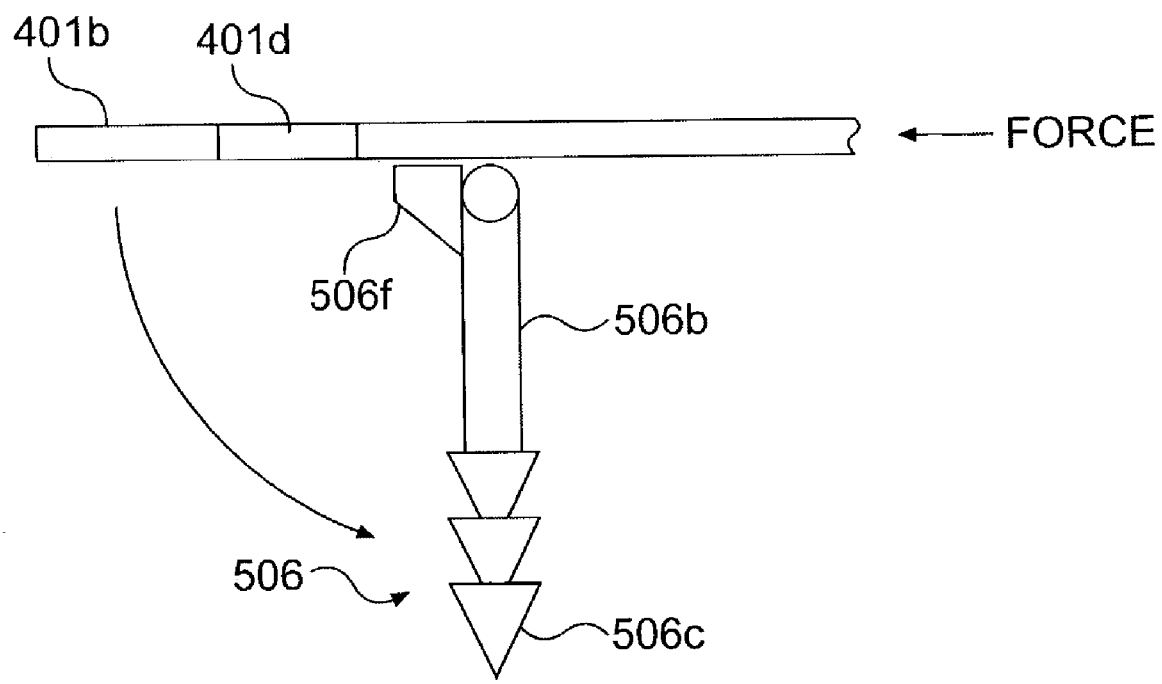

FIGS. 58 and 59 show fastener 506 in relation to ejector arm 401b. Ejector arm 401b is provided with an opening 401d that interacts with tab 506f. End effector 401 is provided with a push wire (not shown) that provides a pushing force onto ejector arm 401b. As arm 401b is moved distally, the trailing edge of window 401d contacts tab 506f causing shaft 506b to rotate into position to mate with female fastener part 508.

Figure 55:
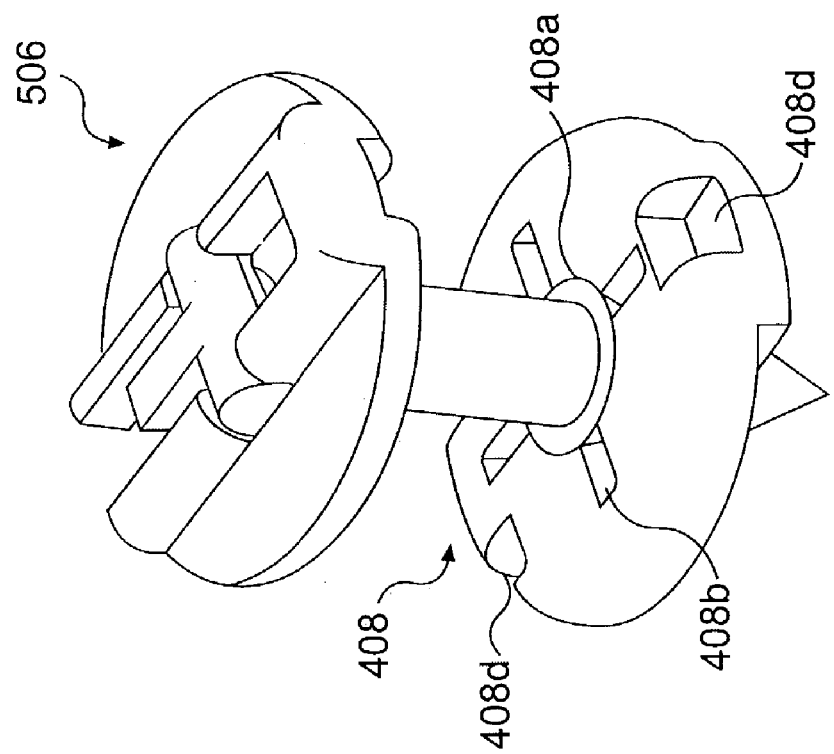
FIGS. 54 and 55 are perspective views of the hinged male fastener part of FIGS. 52 and 53 mated with a female fastener part.
Figure 54:
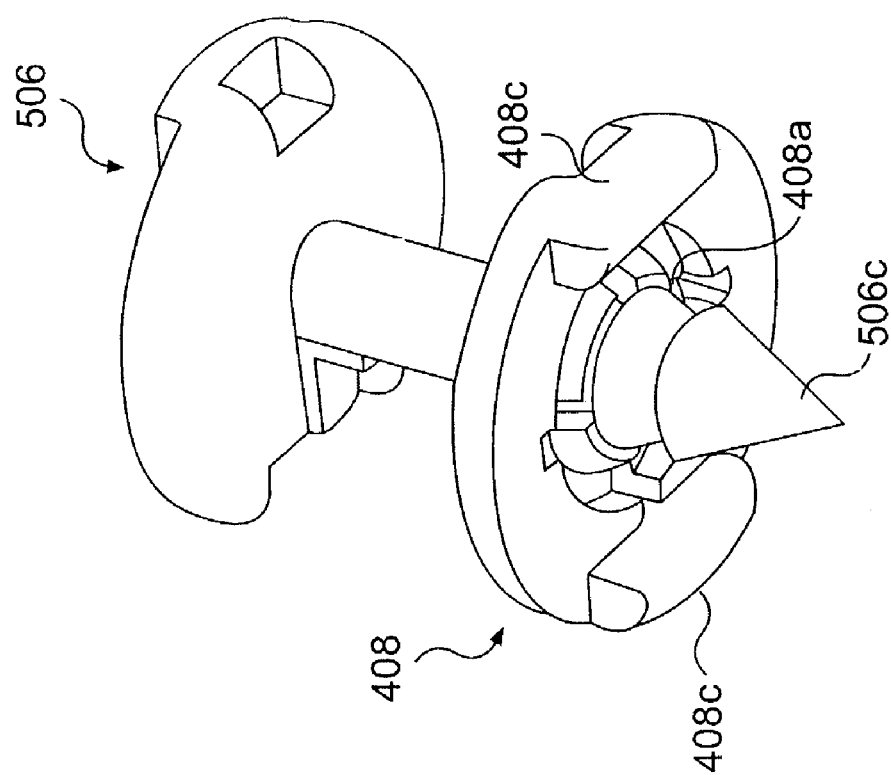

FIGS. 54 and 55 show male fastener 506 of FIGS. 52 and 53 mated with a female fastener 408. Female fastener 408 includes a central hole 408a into which tip 506c of male fastener 506 is capable of entering. Four radial strain relief slots 408b are provided to allow for barbed tip 406c to more easily slide into and mate with female connector 408. Two ribs 408c are provided on a side of female fastener 408 opposite the side through which shaft 506b enters to provide for further structural support within the fastener. Female fastener 408 also has three indentations 408d around the periphery on the side opposite the side containing ribs 408c to allow for fastener 408 to be held in place at the distal end of actuator arm 402 of end effector 400, as best shown in FIG. 49. As shown in FIG. 49, actuator arm includes fingers 450 corresponding to indentations 408d to hold fastener 408 in place. These fingers 450 will release from fastener 408 once fastener 408 mates with a male fastener part.

Figure 57:
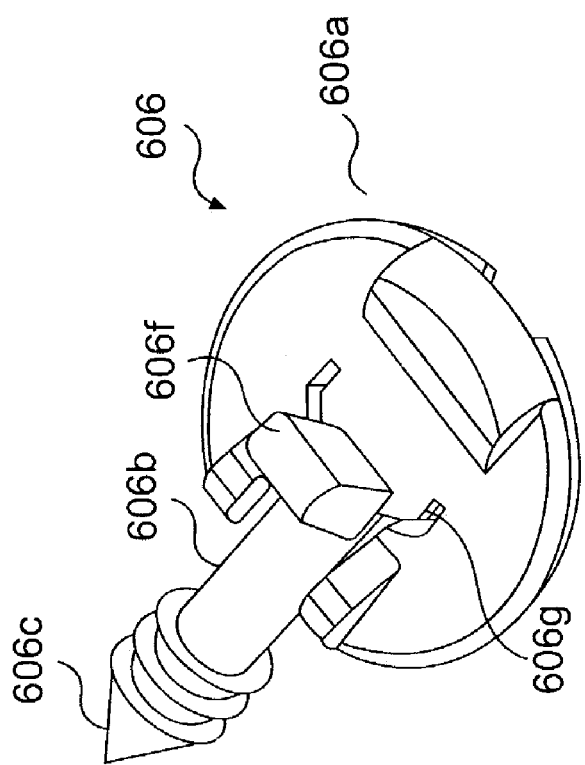
FIGS. 56 and 57 are perspective views of an alternative embodiment of a hinged male fastener.
Figure 56:
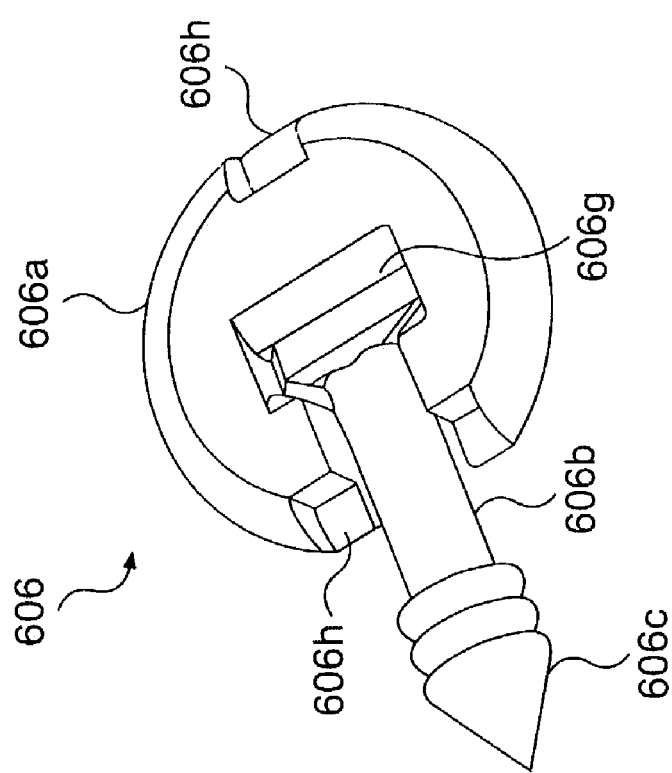

FIGS. 56 and 57 show a further embodiment of a male fastener 606 to be used in connection with end effector 400. In this embodiment, male fastener 606 includes a base 606a and a shaft 606b having a tip 606c that are similar in most respects to those already described. Male fastener 606, however, includes an alternative mechanism 606g for providing pivotal movement of shaft 606b relative to base 606a. Mechanism 606g is in the form of a living hinge. In other words, shaft 606b is formed to connects with base 606a through a thinned out portion of biocompatible material that has sufficient flexibility/bending to permit shaft 606b to pivot relative to base 606a, yet not disconnect from base 606a. Like the prior described embodiment, male fastener 606 includes a deployment tab 606f at the base of shaft 606b. In operation, as male fastener 606 is moved into position at the distal end of effector arm 401, tab 606d would come into contact with a surface on arm 401 that would then apply force to tab 606f, causing shaft 606b to rotate into a deployed position. Male fastener 606 also includes a plurality of indentations or slots 606h that allow fastener 606 to be held in place at the distal end of effector arm 401, similar to slots 408d of female fastener 408 and corresponding fingers 450 of arm 402.

FIGS. 50 and 51 show certain internal portions of actuator arms 401, 402. For example, each arm 401, 402 of end effector 400 includes an ejector arm 401b, 402b and a frame member 401c, 402c, respectively. Frame members 401c, 402 serve to hold the male and female fasteners respectively in place prior to locking, as shown in FIG. 50. In that position, arms 401b, 402b are in a proximal position relative to corresponding members 401c, 402c. FIG. 51 shows the male and female fasteners in lacking relation and being ejected from the end effector. To eject the locked fastener, arms 401b, 402b move distally relative to corresponding members 401c, 402c in a sliding motion.

As arms 410b, 402b force the locked fastener off of end effector 400, a shearing mechanism 410 positioned at the distal end of actuator arm 402 and beneath female connector 408 will sever tip 406c of the male fastener. That tip first passes through an opening 412 when the male and female fasteners mate. As the coupled fastener is released from end effector 400 by ejector arms 401b, 402b, the tip is severed by the distal end of member 402c by the tip, at a detent position, being forced against an edge of opening 412 and pulled away from the fastener. This can be made possible by manufacturing the male fastener part with thinned shaft regions at the detent positions between the barbs so that the portion of the tip protruding through the female fastener is more easily pulled away from the shaft. Positioned inside the opening 412 can be a sharp surface, for example a blade, to shear the tip of the male fastener shaft. Other suitable shearing mechanisms that could fit into the effector arm may be used.

With a multiple barbed fastener, the shearing device shears off only the portion of the shaft that protrudes through the opening in the female fastener. For example, if the female fastener were positioned above barb 406d-2 at detent position 406c-1, then only barb 406d-1 would be severed from the shaft. The shearing mechanism is positioned proximate the female fastener so that the sharing mechanism removes as much of the shaft tip as possible but still leaves enough of the tip that is necessary to keep the fastener together. The removal of the shaft tip by the shearing mechanism reduces trauma to the patient that otherwise may be caused by a sharp tip.

In operation, actuator arms 401, 402 pivoted together so that the shaft of a male fastener insert into the opening in a female fastener. Unlike prior fasteners having a single barb, there was no possibility to adjust the fastener either to alter the pressure applied by the fastener to the tissue or to vary with the thickness of tissue to be fastened. By adding multiple barbs and corresponding detent positions, the fastener can be used to fasten various thicknesses of tissue and can allow a physician to adjust the amount of pressure applied to the tissue by the fastener.

There have been described and illustrated herein several embodiments of a flexible endoscopic surgical instrument for invagination and fundoplication. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

What is claimed is:

1. A tissue fastener used to join multiple tissue layers, comprising:
   a male fastener part including a base and a shaft pivotally connected to the base; and
   a female fastener part configured to engage with the shaft of the male fastener part in a direction from a distal end of the shaft to a proximal end of the shaft,
   wherein the distal end of the shaft comprises a sharp point, and
   wherein the shaft is connected to the base through a material having sufficient flexibility to permit the shaft to pivot relative to the base.

2. A tissue fastener according to claim 1, wherein the shaft is pivotally connected to the base by a hinge.

3. A tissue fastener according to claim 1, wherein the shaft includes a tab receivable in a slot formed in the base so as to rotatably attach the shaft to the base.

4. A tissue fastener according to claim 3, wherein the tab is positioned at a proximal end of the shaft.

5. A tissue fastener according to claim 1, wherein the shaft is configured to move between a first position in which the shaft is positioned in substantially the same plane as the base and a second position in which the shaft is positioned substantially perpendicular to the base.

6. A tissue fastener according to claim 1, wherein the male and female fastener parts are configured to lock to each other.

7. A tissue fastener according to claim 1, wherein the female fastener part includes an opening for receiving a distal end of the shaft.

8. A tissue fastener according to claim 7, wherein the shaft includes a barbed distal end.

9. A tissue fastener according to claim 7, wherein the female fastener part includes at least one radial strain relief slot extending from the opening.

10. A tissue fastener according to claim 7, wherein the female fastener part includes at least one rib for providing structural support, the rib formed on a side opposite to the side from which the distal end of the shaft enters.

11. A method of fastening multiple tissue layers, comprising:
providing a tissue fastener comprising:
a male fastener part including a base and a shaft pivotally connected to the base; and
a female fastener part configured to mate with the shaft of the male fastener part;
positioning the male fastener part adjacent a first side of the multiple tissue layers;
after the positioning step, passing the shaft of the male fastener part through the multiple tissue layers; and
mating the shaft of the male fastener part with the female fastener part on a second side of the multiple tissue layers, so that the multiple tissue layers are fastened between the male and female fastener parts.

12. A method of fastening multiple tissue layers, comprising:
providing a tissue fastener comprising:
a male fastener part including a base and a shaft pivotally connected to the base; and
a female fastener part configured to mate with a portion of the male fastener part;
rotating the shaft from a first position in which the shaft is in substantially the same plane as the base to a second position in which the shaft is substantially perpendicular to the base;
positioning the male and female fastener parts adjacent each side of the multiple tissue layers so that the multiple tissue layers are placed between the male and female fastener parts;
passing the shaft of the male fastener part through the multiple tissue layers; and
mating the shaft of the male fastener part with the female fastener part.

13. A method according to claim 11, wherein the mating step includes advancing the shaft into an opening formed in the female fastener part.

14. A method according to claim 13, wherein the female fastener part includes at least one radial strain relief slot extending from the opening.

15. A method of fastening multiple tissue layers, comprising:
providing a tissue fastener comprising:
a male fastener part including a base and a shaft pivotally connected to the base; and
a female fastener part configured to mate with a portion of the male fastener part;
positioning the male and female fastener parts adjacent each side of the multiple tissue layers so that the multiple tissue layers are placed between the male and female fastener parts;
passing the shaft of the male fastener part through the multiple tissue layers;
mating the shaft of the male fastener part with the female fastener part, the mating step including advancing the shaft into an opening formed in the female fastener part; and
shearing off a portion of the shaft protruding out of the opening of the female fastener part.

16. A method according to claim 11, wherein the passing step includes perforating the multiple tissue layers by a sharp distal end of the shaft.

17. A method of fastening multiple tissue layers, comprising:
providing a tissue fastener comprising:
a male fastener part including a base and a shaft pivotally connected to the base; and
a female fastener part configured to mate with a portion of the male fastener part;
positioning the male and female fastener parts adjacent each side of the multiple tissue layers so that the multiple tissue layers are placed between the male and female fastener parts;
passing the shaft of the male fastener part through the multiple tissue layers; and
mating the shaft of the male fastener part with the female fastener part,
wherein the multiple tissue layers include an esophageal wall and a gastric fundus wall.

18. A tissue fastener used to join multiple tissue layers, comprising:
a male fastener part including a base and a shaft pivotally connected to the base at a proximal end of the shaft; and
a female fastener part configured to engage with the shaft of the male fastener part in a direction from a distal end of the shaft to the proximal end of the shaft,
wherein the male and female fastener parts are disconnected from each other prior to mating with each other, and
wherein the shaft is connected to the base through a material having sufficient flexibility to permit the shaft to pivot relative to the base.

19. A tissue fastener according to claim 18, wherein the distal end of the shaft comprises a sharp point.

20. A tissue fastener according to claim 18, wherein the shaft is pivotally connected to the base by a hinge.

21. A tissue fastener according to claim 18, wherein the shaft includes a tab receivable in a slot formed in the base so as to rotatably attach the shaft to the base.

22. A tissue fastener according to claim 21, wherein the tab is positioned at a proximal end of the shaft.

23. A tissue fastener used to join multiple tissue layers, comprising:
a male fastener part including a base and a shaft pivotally connected to the base; and
a female fastener part configured to mate with the shaft of the male fastener part,
wherein the male and female fastener parts are disconnected from each other prior to mating with each other, and wherein the shaft is configured to move between a first position in which the shaft is positioned in substantially the same plane as the base and a second position in which the shaft is positioned substantially perpendicular to the base.

24. A tissue fastener according to claim 18, wherein the male and female fastener parts are configured to lock to each other.

25. A tissue fastener according to claim 18, wherein the female fastener part includes an opening for receiving the distal end of the shaft.

26. A tissue fastener according to claim 25, wherein the shaft includes a barbed distal end.

27. A tissue fastener according to claim 25, wherein the female fastener part includes at least one radial strain relief slot extending from the opening.

28. A tissue fastener according to claim 25, wherein the female fastener part includes at least one rib for providing structural support, the rib formed on a side opposite to the side from which the distal end of the shaft enters.

* * * * *